US009322051B2

(12) United States Patent
Sood et al.

(10) Patent No.: US 9,322,051 B2
(45) Date of Patent: Apr. 26, 2016

(54) PROBING OF BIOLOGICAL SAMPLES

(71) Applicant: GENERAL ELECTRIC COMPANY, Schenectady, NY (US)

(72) Inventors: Anup Sood, Clifton Park, NY (US); Arunkumar Natarajan, Niskayuna, NY (US); Michael James Rishel, Saratoga Springs, NY (US); Michael John Gerdes, Albany, NY (US)

(73) Assignee: General Electric Company, Niskayuna, NY (US)

( * ) Notice: Subject to any disclaimer, the term of this patent is extended or adjusted under 35 U.S.C. 154(b) by 397 days.

(21) Appl. No.: 14/047,233

(22) Filed: Oct. 7, 2013

(65) Prior Publication Data

US 2015/0099650 A1    Apr. 9, 2015

(51) Int. Cl.
*C12Q 1/68* (2006.01)
*G01N 33/68* (2006.01)
*G01N 33/53* (2006.01)
*G01N 33/533* (2006.01)
*G01N 33/542* (2006.01)
*G01N 33/543* (2006.01)

(52) U.S. Cl.
CPC .............. *C12Q 1/6825* (2013.01); *G01N 33/53* (2013.01); *G01N 33/533* (2013.01); *G01N 33/542* (2013.01); *G01N 33/6854* (2013.01); *C12Q 2523/319* (2013.01)

(58) Field of Classification Search
CPC ........... C12Q 1/6825; C12Q 2523/319; G01N 33/6854; G01N 33/53; G01N 33/533; G01N 33/542
See application file for complete search history.

(56) References Cited

U.S. PATENT DOCUMENTS

| 6,068,979 | A  | 5/2000  | Akhavan-Tafti   |
|-----------|----|---------|-----------------|
| 7,629,125 | B2 | 12/2009 | Sood et al.     |
| 7,741,046 | B2 | 6/2010  | Larsen et al.   |
| 8,036,462 | B2 | 10/2011 | Can et al.      |
| 8,060,348 | B2 | 11/2011 | Cline et al.    |
| 8,131,476 | B2 | 3/2012  | Cline et al.    |
| 8,320,655 | B2 | 11/2012 | Sarachan et al. |
| 8,369,600 | B2 | 2/2013  | Can et al.      |
| 2006/0063186 | A1 | 3/2006 | Benson et al.   |
| 2008/0032321 | A1 | 2/2008 | Ginty et al.    |
| 2008/0118944 | A1 | 5/2008 | Larsen et al.   |
| 2009/0221718 | A1 | 9/2009 | Ruoslahti et al.|
| 2009/0245610 | A1 | 10/2009| Can et al.      |

(Continued)

FOREIGN PATENT DOCUMENTS

WO    2010042525  A9    4/2010
WO    2012143556  A2    10/2012

OTHER PUBLICATIONS

Höbartner et al., "Review—Recent Advances in DNA Catalysis", Biopolymers, vol. 87, No. 5-6, 2007, pp. 279-292.

(Continued)

*Primary Examiner* — Jeremy C Flinders
(74) *Attorney, Agent, or Firm* — Eileen B. Gallagher

(57) ABSTRACT

Disclosed are high throughput methods of probing multiple targets in a biological sample where the recurrent time-consuming antibody incubation steps and individual signal modification and activation steps are replaced by simultaneous hybridization of biomarkers and sequential detection by combining signal removal and activation into a single step. Also disclosed are images obtained by such methods.

21 Claims, 4 Drawing Sheets

(56) References Cited

U.S. PATENT DOCUMENTS

| | | |
|---|---|---|
| 2010/0120043 A1 | 5/2010 | Sood et al. |
| 2011/0091081 A1 | 4/2011 | Sarachan et al. |
| 2011/0091091 A1 | 4/2011 | Sarachan et al. |
| 2011/0092381 A1 | 4/2011 | Sood et al. |
| 2012/0100560 A1 | 4/2012 | Searson et al. |
| 2012/0208223 A1 | 8/2012 | Kumar et al. |
| 2013/0044933 A1 | 2/2013 | Kenny |
| 2013/0065782 A1 | 3/2013 | Ostroff et al. |
| 2013/0165330 A1 | 6/2013 | Natarajan et al. |

OTHER PUBLICATIONS

Menge et al., "Coumarin-Caged dG for Improved Wavelength-Selective Uncaging of DNA", Organic Letters, vol. 13, No. 17, Sep. 2, 2011, pp. 4620-4623.

Leriche et al., "Cleavable Linkers in Chemical Biology", Bioorganic & Medicinal Chemistry, vol. 20, Issue 2, Jan. 15, 2012, pp. 571-582.

Bai et al., "Photocleavage of a 2-nitrobenzyl linker bridging a fluorophore to the 5' end of DNA", Proc Natl Acad Sci USA, vol. 100, No. 2, Jan. 21, 2003, pp. 409-413.

Klán et al., "Photoremovable Protecting Groups in Chemistry and Biology: Reaction Mechanisms and Efficacy", Chemical Reviews, vol. 113, Issue 1, 2013, pp. 119-191.

Miller, et al. "Photopolymerization Studies" Macromolecules 2008, vol. 7, No. 2, 1974, pp. 179-187.

Eaton, "Dye-Sensitized Photpolymerization: Activation by TrialkylbenzyLstannanes" Photographic Scientists and Engineers, 1979, vol. 23, pp. 150-154.

Eaton, "Electron Transfer Processes in Imaging", Topics in Current Chemistry, Springer-Verlag: Berlin, 1990, vol. 156, pp. 199-225.

Eaton, "Electron Transfer Induced Photogragmentation as a Route to Free Radicals" Pure & Appl. Chem., 1984, vol. 56, No. 9, pp. 1191-1202.

PCT Search Report and Written Opinion from corresponding PCT Application No. PCT/US2014/058986 dated Jan. 8, 2015.

Han et al., "An Approach to Multiplexing and Immunosorbent Assay with Antibody—Oligonucleotide Conjugates", Bioconjugate Chemistry, vol. 21, No. 12, 2010, pp. 2190-2196.

PROBING OF BIOLOGICAL SAMPLES

BACKGROUND

Various methods may be used in biology and in medicine to observe different targets in a biological sample. For example, analysis of proteins in histological sections and other cytological preparations may be performed using the techniques of histochemistry, immunohistochemistry (IHC), or immunofluorescence. Analysis of proteins in biological samples may also be performed using solid-state immunoassays, for example, using the techniques of western blots, or using cell-based assays that can be performed, for example, by using flow cytometry.

Many of the current techniques may detect only a few targets at one time (such as IHC or fluorescence-based Western blots where number of targets detectable is limited by the fluorescence-based detection system) in a single sample. Further analysis of targets may require use of additional biological samples from the source, limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis.

Methods of iteratively analyzing an individual sample are described in U.S. Pat. No. 7,629,125 and U.S. Pat. No. 7,741,046. In particular, U.S. Pat. No. 7,741,046 provides methods of detecting multiple targets in a biological sample that involve the use of oxidation for inactivating signal generators (e.g., for bleaching fluorescent dyes.) The oxidation reaction is accomplished by using oxidizing reagents, such as hydrogen peroxide. Additionally, a signal can be inactivated by continuous exposure of the signal generator to irradiation, i.e., by photobleaching. Similar to signal inactivation by oxidation, this process can be lengthy and may not proceed to completion, resulting in reduced signal-to-noise ratio. In addition, continued exposure of sample to irradiation may damage the biological sample.

However, often these methods of biomarker analysis are limited to detection of a relatively few markers (up to four) due to spectral overlap among available fluorophores and complex imaging systems requirements for hyperspectral imaging and deconvolution of spectra. For example, a multiplex immunofluorescence platform may utilize an antibody cycling process whereby a sample is stained with three antibodies per cycle, imaged, and restained with another set of antibodies after the signal from the first set of antibodies has been removed. This approach may be limited though, while the platform allows for the detection of multiple biomarkers, the repeated antibody incubations and destaining steps, which can range from 30 to 60 minutes per cycle, add a significant amount of time to the overall process.

US patent applications US20100120043A1 and US20110092381A1 describe a method of simultaneous hybridization of probes followed by sequential detection. After hybridization and detection of first set of probes the method includes steps of modifying the signal from the first set of probes followed by generating the signal from a second set of probes. To reduce process time, it would be of benefit to achieve the modification of one set of signal and activation of the next in the same step.

As such a method which provides a high throughput technology where repeated time-consuming probe incubation steps are diminished is desirable.

BRIEF DESCRIPTION

Disclosed herein are novel methods for a high throughput technology where the recurrent time-consuming antibody incubation steps and individual signal modification and activation steps are replaced by simultaneous hybridization of biomarkers and sequential detection by combining signal removal and activation into a single step.

In some embodiments, a method of probing multiple targets in a biological sample comprising a number of steps is disclosed. The steps include providing a biological sample containing multiple targets; binding a set of probes to the multiple targets wherein two or more of the probes comprise independently a binder capable of specific binding to at least one target in the biological sample, a signal generator (SG), a linker which couples the SG to the binder, and a masking agent coupled to the SG which quenches the signal of the SG. At least one linker and one masking agent in the set of probes form a linker-mask pair that is orthogonal to other pairs. Subsequent steps further comprise detecting at least one signal from at least one signal generator from the set of probes bound in the preceding step; contacting the sample comprising the bound probes with a chemical agent, electromagnetic radiation or a combination thereof and simultaneously deactivating the at least one signal generator by cleavage of a linker bound to the signal generator and activating at least one signal generator from the set of probes previously quenched by a masking agent. The linker and masking agent are linker-mask pairs. The newly activated signal may be detected and the activation/deactivation and detection steps may be repeated.

Also disclosed are a series of at least two images depicting optically labeled biological targets wherein the images are obtained in the aforementioned process.

DETAILED DESCRIPTION

Figure 1:
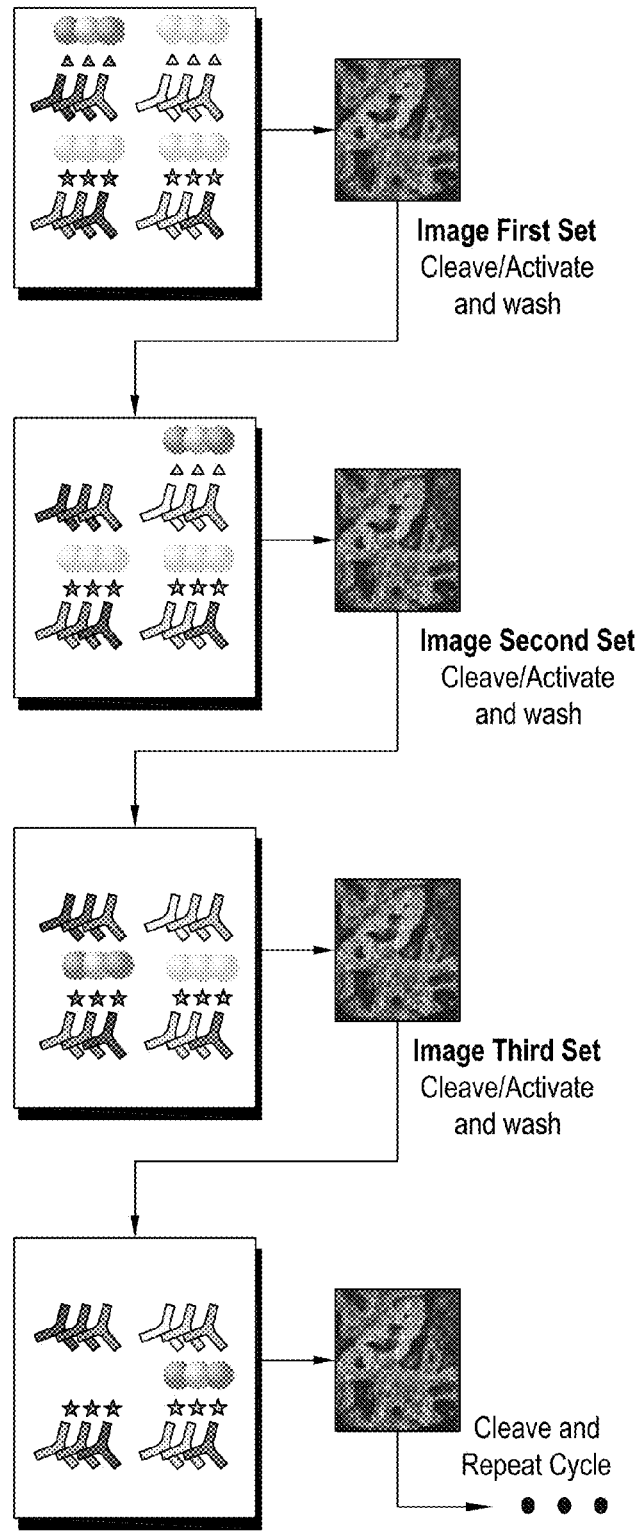
FIG. 1 is a schematic representation showing simultaneous and sequential analysis of the multiple biomarkers; 4 sets of three antibody probes analyzed in a total of four imaging rounds.

The singular forms "a" "an" and "the" include plural references unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

As used herein, the term "alkyl" refers to saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.). In certain embodiments, a straight chain or branched chain alkyl has 6 or fewer carbon atoms in its backbone (e.g., $C_1$-$C_6$ for straight chain, $C_3$-$C_6$ for branched chain) or 4 or fewer carbon atoms in its backbone (e.g., $C_1$-$C_4$ for straight chain, $C_3$-$C_4$ for branched chain). The term "$C_1$-$C_6$" alkyl refers to alkyl groups containing 1 to 6 carbon atoms. The term "$C_1$-$C_4$" alkyl refers to alkyl groups containing 1 to 4 carbon atoms. Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, (C1-C4)alkyl, (C1-C4)alkoxy, amino (including (C1-C4)alkylamino and (C1-C4)dialkylamino), hydroxyl, cyano, halogen, or nitro. Cycloalkyls can be further substituted, e.g., with the substituents described above.

As used herein, the term "alkenyl" refers to unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups. Moreover, the term "alkenyl" includes both "unsubstituted alkenyls" and "substituted alkenyls," the latter of which refers to alkenyl moieties having substituents replacing a hydrogen on one or more carbons of the hydrocarbon backbone. Such substituents can include, for example, (C1-C4)alkyl, (C1-C4)alkoxy, amino (including (C1-C4)alkylamino and (C1-C4)dialkylamino), hydroxyl, cyano, halogen, or nitro.

As used herein, the term "alkynyl" refers to unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), or branched-chain alkynyl groups. Moreover, the term "alkynyl" includes both "unsubstituted alkynyls" and "substituted alkynyls," the latter of which refers to alkynyl moieties having substituents replacing a hydrogen on one or more carbons of the hydrocarbon backbone. Such substituents can include, for example, (C1-C4)alkyl, (C1-C4)alkoxy, amino (including (C1-C4)alkylamino and (C1-C4)dialkylamino), hydroxyl, cyano, halogen, or nitro.

As used herein, the term "alkoxy" refers to substituted and unsubstituted alkyl, alkenyl, and alkynyl groups covalently linked to an oxygen atom. Examples of alkoxy groups include, but are not limited to, methoxy, ethoxy, isopropyloxy, propoxy, butoxy, and pentoxy groups. In certain embodiments, a straight chain or branched chain alkoxy has 4 or fewer carbon atoms in its backbone (e.g., $C_1$-$C_4$ for straight chain, $C_3$-$C_4$ for branched chain). The term "$C_1$-$C_4$" alkyl refers to alkyl groups containing 1 to 4 carbon atoms.

As used herein, the term "amine" or "amino" refers to compounds or substituents where a nitrogen atom is covalently bonded to at least one carbon or heteroatom. The term includes "alkyl amino" which comprises groups and compounds wherein: the nitrogen is bound to at least one additional alkyl group. The term "dialkyl amino" includes groups wherein: the nitrogen atom is bound to at least two additional alkyl groups. In certain embodiments, these alkyl groups have 4 or fewer carbon atoms in their backbone (e.g., $C_1$-$C_4$ for straight chain, $C_3$-$C_4$ for branched chain). The term (C1-C4)alkylamino refers to groups and compounds, wherein the nitrogen is bound to at least one additional C1-C4 alkyl group. The term "(C1-C4)dialkylamino" refers to groups and compounds, wherein the nitrogen is bound to at least two additional C1-C4 alkyl groups.

As used herein, the term "aryl" refers to groups, e.g., 5- and 6-membered single-ring aromatic groups, that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heteroaryls" or "heteroaromatics." The aromatic ring can be substituted at one or more ring positions with such substituents as described above, as for example, (C1-C4)alkyl, (C1-C4)alkoxy, amino (including (C1-C4)alkylamino and (C1-C4)dialkylamino), hydroxyl, cyano, halogen, or nitro. Aryl groups can also be fused or bridged with alicyclic or heterocyclic rings which are not aromatic so as to form a polycycle (e.g., tetralin). The term heteroaryl includes unsaturated cyclic compounds such as azirine, oxirene, dithiete, pyrroline, pyrrole, furan, dihydrofuran, dihydrothiophene, thiophene, pyrazole, imidazole, oxazole, thiazole, isothiazole, 12,2,3-triazole, 1,2,4, triazole, dithiazole, tetrazole, pyridine, pyran, pyrimidine, pyran, thiapyrane, diazine, thiazine, dioxine, triazine and tetrazene.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab').sub.2, or Fab'). In addition, aggregates, polymers, and conjugates of immunoglobulins or their fragments may be used where appropriate so long as binding affinity for a particular molecule is substantially maintained.

As used herein, the term "binder" refers to a molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens. A suitable binder may be selected depending on the sample to be analyzed and the targets available for detection. For example, a target in the sample may include a ligand and the binder may include a receptor or a target may include a receptor and the binder may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "bleaching" refers generally to the process wherein the optical signal from a signal generator is removed or modified to render the signal undetectable upon exposure to light that was previously capable of exciting the signal generator.

As used herein, the term "linker" refers to a specific type of chemical linkage which couples the signal generator to the binder and may be specifically designed to be cleaved, under specific reaction conditions in a manner that enables deactivation or removal of the signal generator attached to the linker and concurrent activation of a second signal generator bond to a masking agent. The linker may be cleaved using a photoinduced or chemical process. As such the linker may be referred to as a cleavable bridging molecule connecting the binder, such as an antibody or nucleic acid, to the signal generator which may be a fluorescent dye.

As used herein the term "masking agent" refers to a molecule that holds the signal generator, for example a fluorescent dye, in a quenched state until activation through a photo or chemically induced process. The masking agent and linker are formulated such that they may be employed to work in parallel with one another, allowing simultaneous cleavage of a particular linker and masking agent resulting in the activation of an initially masked signal generator and deactivation or removal of the initially active signal generator bound to a binder and attached through a linker. In some embodiments, the masking group is a quencher linked to the flour via a linker. In other embodiments the masking agent comprises a chemical moiety that transitions the signal generator into a quenched state.

As used herein, the term "biological sample" refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, cells isolated from mammals including, humans and cell organelles. Biological samples also may include sections of the biological sample including tissues (e.g., sectional portions of an organ or tissue). Biological samples may also include extracts from a biological sample, for example, an antigen or a nucleic acid from a biological fluid (e.g., blood or urine). Biological samples may comprise proteins, carbohydrates or nucleic acids.

A biological sample may be of prokaryotic origin, archaeal origin, or eukaryotic origin (e.g., insects, protozoa, birds, fish, and reptiles). In some embodiments, the biological sample is mammalian (e.g., rat, mouse, cow, dog, donkey, guinea pig, or rabbit). In certain embodiments, the biological sample is of primate origin (e.g., example, chimpanzee, or human).

As used herein, the term "enzyme" refers to a protein molecule that can catalyze a chemical reaction of a substrate. In some embodiments, a suitable enzyme catalyzes a chemical reaction of the substrate to form a reaction product that can bind to a receptor (e.g., phenolic groups) present in the sample. A receptor may be exogenous (that is, a receptor extrinsically adhered to the sample or the solid-support) or endogenous (receptors present intrinsically in the sample or the solid-support). Examples of suitable enzymes include peroxidases, oxidases, phosphatases, esterases, and glycosidases. Specific examples of suitable enzymes include horseradish peroxidase, alkaline phosphatase, β-D-galactosidase, lipase, and glucose oxidase.

As used herein, the term "enzyme substrate" refers to a chemical compound that is chemically catalyzed by an enzyme to form a reaction product. In some embodiments, the reaction product is capable of binding to a receptor present in the sample. In some embodiments, enzyme substrates employed in the methods herein may include non-chromogenic or non-chemiluminescent substrates. A signal generator may be attached to the enzyme substrate as a label.

As used herein, the term "electron transfer reagent" refers to a reagent that can engage in a photoreaction with a molecule capable of undergoing photoexcitation. This term also refers to a composition comprising a reagent that can engage in a photoreaction with a molecule capable of undergoing photoexcitation. In some embodiments, the molecule capable of undergoing photoexcitation may be a signal generator. In some embodiment, the electron transfer reagent may donate an electron to the signal generator in the course of a photoreaction. In alternative embodiments, the electron transfer reagent may accept an electron from the signal generator in the course of a photoreaction.

In some embodiments, the electron transfer reagent donating an electron to the signal generator in the course of a photoreaction may be a borate salt. In a further embodiment, the borate salt is triphenylbutyl borate.

In alternative embodiments, the electron transfer reagent accepting an electron from the photoexcited molecule may be an onium salt [e.g., diphenyliodonium hexafluorophosphate (DPI) or dimethylphenacylsulfonium tetrafluoroborate (DMPS)], or tetrabutylammonium butyltriphenylborate (TBAB).

As used herein, the term "fluorophore" or "fluorescent signal generator" refers to a chemical compound, which when excited by exposure to a particular wavelength of light, emits light of a longer wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446;

Malachite Green isothiocyanate; 4-methylumbelliferone; ortho cresolphthalein; nitrotyro sine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, cyanines, pyrelium dyes, squaraines, 1,3-dichloro-7-hydroxy-9, 9-dimethyl-2(9H)-Acridinone (DDAO), and dimethylacridinone (DAO). In some embodiments, the fluorophore can be cyanine, rhodamine, BODIPY or 1,3-dichloro-7-hydroxy-9, 9-dimethyl-2(9H)-Acridinone (DDAO) dyes. In a preferred embodiment, the fluorophore is a cyanine dye. In a further embodiment, the cyanine dye is Cy3 or Cy5.

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

As used herein, the terms "irradiation" or "irradiate" refer to act or process of exposing a sample or a solution to non-ionizing radiation. In some embodiments, the non-ionizing irradiation has wavelengths between 300 nm and 1.3 µm. In preferred embodiments, the non-ionizing radiation is between 300-700 nm in wavelength. Irradiation may be accomplished by exposing a sample or a solution to a radiation source, e.g., a lamp, capable of emitting radiation of a certain wavelength or a range of wavelengths. In some embodiments, a molecule capable of undergoing photoexcitation is photoexcited as a result of irradiation. In some embodiments, the moiety capable of undergoing photoexcitation is a linker group joining the probe and the signal generator. In some embodiments the moiety capable of undergoing photoexcitation is a masking group, quenching the fluorescence of dye.

Optical filters may be used to restrict irradiation of a sample or a solution to a particular wavelength or a range of wavelengths. In some embodiments, the optical filters may be used to restrict irradiation to a narrow range of wavelengths for selective photoexcitation of one or more molecules capable of undergoing photoexcitation. The term "selective photoexcitation" refers to an act or a process, whereby one or more molecules capable of undergoing photoexcitation are photoexcited in the presence of one or more other molecules capable of undergoing photoexcitation that remain in the ground electronic state after irradiation.

In some embodiments, the wavelength selected for photo excitation is based on the molecule or moiety to be excited. For example, in some embodiments the molecule capable of undergoing photoexcitation may be a nitrophenolic moiety. In this embodiment, irradiation may be limited to a range of wavelengths from 200-400 nm as the nitorphenolic moiety is excitable within this range. In alternative embodiments, irradiation of a sample at a specific wavelength may also be accomplished by using a laser.

As used herein, the term "peroxidase" refers to an enzyme class that catalyzes an oxidation reaction of an enzyme substrate along with an electron donor. Examples of peroxidase enzymes include horseradish peroxidase, cytochrome C peroxidase, glutathione peroxidase, microperoxidase, myeloperoxidase, lactoperoxidase, or soybean peroxidase.

As used herein, the term "peroxidase substrate" refers to a chemical compound that is chemically acted upon by peroxidase to form a reaction product. The peroxidase enzyme may serve to catalyze the chemical transformation in question. In some embodiments, peroxidase substrates employed in the methods herein may include non-chromogenic or non-chemiluminescent substrates. A fluorescent signal generator may be attached to the peroxidase substrate as a label. In some embodiments the signal generator is attached to the peroxidase substrate through a cleavable linker. In some embodiment, the linker is a photocleavable linker.

As used herein, the term, "photoactivated chemical bleaching" or "photoinduced chemical bleaching" (PICB) refers to an act or a process whereby a signal generated by a signal generator is modified in the course of a photoreaction. In certain embodiments, the signal generator is irreversibly modified.

In some embodiments, the signal is diminished or eliminated as a result of photoactivated chemical bleaching. In some embodiments, the signal generator is completely bleached, i.e., the signal intensity decreases by about 100%. In some embodiments, the signal is an optical signal, and the signal generator is an optical signal generator. The term "photoactivated chemical bleaching" is meant to exclude photobleaching, or loss of signal (e.g., fluorescent signal) that may occur in the absence of electron transfer reagent, e.g., after continued irradiation of a signal generator, such as a fluorophore, or after its continued exposure to light.

As used herein, the term "photoexcitation" refers to an act or a process whereby a molecule transitions from a ground electronic state to an excited electronic state upon absorption of radiation energy, e.g. upon photo-irradiation. Photoexcited molecules can participate in chemical reactions, e.g., rearrangements to undergo cleavage. In some embodiments, a molecule capable of undergoing photoexcitation is a linker, e.g. a nitrophenol linker. In other embodiments, the molecule undergoing photoexcitation is a mask. In yet, other embodiments both linker and mask undergo photoexcitation at the same time.

As used herein, the term "probe" refers to an agent having a binder and a label, such as a signal generator attached to an antibody. In some embodiments, the binder and the label (signal generator or the antibody) are embodied in a single entity. The binder and the label may be attached directly (e.g., via a fluorescent molecule incorporated into the binder) or indirectly (e.g., through a linker) and applied to the biological sample in a single step. In alternative embodiments, the binder and the label are embodied in discrete entities (e.g., a primary antibody capable of binding a target and an enzyme or a signal generator-attached to secondary antibody capable of binding the primary antibody). When the binder and the label (signal generator or the antibody) are separate entities they may be applied to a biological sample in a single step or multiple steps. As used herein, the term "fluorescent probe" refers to an agent having a binder coupled to a fluorescent signal generator. In some embodiments, the probe may comprise an optical signal generator, such that the signal detected is an optical signal. In some embodiments, the probe may comprise a fluorescent signal generator, such that the signal detected is a fluorescent signal.

As such multiple methodologies may be used for the detection of the probe based on the signal generated by the probe. For example the detection system may include an electron spin resonance (ESR) detection system, a charge coupled device (CCD) detection system (e.g., for radioisotopes), a fluorescent detection system, an electrical detection system, a photographic film detection system, a chemiluminescent detection system, an enzyme detection system, an atomic force microscopy (AFM) detection system (for detection of microbeads), a scanning tunneling microscopy (STM) detection system (for detection of microbeads), an optical detection system, a near field detection system, or a total internal reflection (TIR) detection system. It is to be noted that not all these signals can be quenched by masking, e.g. microbeads and radioisotopes. In such cases these signal may only be used to detect the first set of targets prior to removal and activation of a different signal that is capable of being masked.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, or an electrical signal. Examples of signal generators may include one or more of a chromophore, a fluorophore, or a Raman-active tag. As stated above, with regard to the probe, the signal generator and the binder may be present in a single entity (e.g., a target binding protein with a fluorescent label) in some embodiments. Alternatively, the binder and the signal generator may be discrete entities (e.g., a receptor protein and a labeled-antibody against that particular receptor protein) that associate with each other before or upon introduction to the sample.

In some embodiments, the signal generator may be an optical signal generator. In some embodiments, the optical signal generator may be a fluorescent signal generator, e.g., a fluorophore. In preferred embodiments, the fluorescent signal generator may be a xanthene dye, e.g., fluorescein, rhodamine, naphthofluorescein, etc. In some embodiments, the signal generator, e.g., a fluorophore, may be charged. In one embodiment, the signal generator is an anionic fluorescent dye.

In some embodiments, the signal generator may be an optical signal generator. In some embodiments, the optical signal generator may be a fluorescent signal generator, e.g., a fluorophore. In preferred embodiments, the fluorescent signal generator may be a cyanine dye, e.g., Cy3, Cy5 or Cy7. In some embodiments, the signal generator, e.g., a fluorophore, may be charged. In one embodiment, the signal generator is a cationic fluorescent dye.

As used herein, the term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, glass, or a metallic material. Examples of solid supports include a membrane, a microtiter plate, a bead, a filter, a test strip, a slide, a cover slip, and a test tube.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant ($K_A$) for the target no lower than about $10^5$ $M^{-1}$ under ambient conditions such as a pH of about 6 to about 8 and temperature ranging from about 0° C. to about 37° C.

As used herein, the term "target" refers to the component of a biological sample that may be detected when present in the biological sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

The invention includes embodiments that relate generally to methods applicable in analytical, diagnostic, or prognostic applications such as analyte detection, fluorescence-activated cell sorting (FACS), histochemistry, immunohistochemistry (IHC), immunofluorescence (IF) or fluorescence in situ hybridization (FISH). In some embodiments, the methods disclosed herein may be particularly applicable in histochemistry, immunostaining, immunohistochemistry, immunoassays, immunofluorescence or FISH. In some embodiments, the methods disclosed herein may be particularly applicable in immunoblotting techniques, for example, western blots or immunoassays such as enzyme-linked immunosorbent assays (ELISA).

The disclosed methods relate generally to detection of multiple targets in a single biological sample. In some embodiments, methods of detecting multiple targets in a single biological sample using the same detection channel are disclosed. A channel refers to the specific bandwidth or wavelength range to be detected. The targets may be present on the surface of cells in suspension, on the surface of cytology smears, on the surface of histological sections, on the surface of DNA microarrays, on the surface of protein microarrays, or on the surface of solid supports (such as gels, blots, glass slides, beads, or ELISA plates).

The methods disclosed herein may allow detection of a plurality of targets in the same biological sample. Detecting the targets in the same biological sample may further provide spatial information about the targets in the biological sample. Methods disclosed herein may also be applicable in analytical applications where a limited amount of biological sample may be available for analysis and the same sample may have to be processed for multiple analyses. Methods disclosed herein may also facilitate multiple analyses of solid-state samples (e.g., tissue sections) or samples adhered to a solid support (e.g., blots) without substantially stripping the probes and the targets. Furthermore, the same detection channel may be employed for detection of different targets in the sample, enabling fewer chemistry requirements for analyses of multiple targets. The methods may further facilitate analyses based on detection methods that may be limited in the number of simultaneously detectable targets because of limitations of resolvable signals. For example, using fluorescent-based detection, the number of targets that may be simultaneously detected may be limited to about four as only about four fluorescent signals may be resolvable based on their excitation and emission wavelength properties. In some embodiments, the methods disclosed herein may allow detection of greater than four targets using fluorescence-based detection system.

In some embodiments, the method is a high throughput multiplexing biological assay that functions by creating a variety of orthogonally cleavable linkers and masks that can be cleaved under a defined set of conditions that does not significantly affect the other cleavable binders and masks or the sample. As used herein the term "orthogonal cleavage" refers to regioslective cleavage of two substituents that are cleaved under substantially different reactions conditions (i.e one substituent remains intact during the cleavage of the other). The substituents are groups that may serve as protecting or linking groups which upon certain conditions function as leaving groups or latent leaving groups.

In certain embodiments, the method may provide simultaneous hybridization and subsequent imaging of two sets of antibodies; one set may be modified with fluorescent dyes attached through a cleavable linker, while the other set is modified with masked dyes that can be activated under the same conditions that are used to cleave the dyes from the first set. The second set, of newly activated dyes, may or may not contain a cleavable linker that is stable to the cleavage conditions used for the first set.

In some embodiments, the method includes using linker and active masking chemistries to enable simultaneous incubation and sequential detection of multiple biomarkers eliminating the time-consuming staining/de-staining/washing cycles used in current state-of-the-art multiplexing approaches. The linker may be referred to as a cleavable bridging molecule connecting the biological targeting moiety (antibody or nucleic acid) and the signal generator (fluorescent dye) and the mask which holds the signal generator in a quenched state ("masked") until the activation stimuli is employed. The activation may be through chemical or photo-induced processes.

In certain embodiments the linker and mask may be activated through photochemistry. The "photo-cleavable linker (PCL)" is referred to cleavable bridging molecule connecting the biological targeting moiety (antibody or nucleic acid) and the signal generator (fluorescent dye). The "photo-active mask" is referred to a molecule that holds the fluorescent signal generator in quenched state ("masked") until the activation stimuli (light of specific wavelength) is employed. As such, in certain embodiments, simultaneous multiplexing of biomarkers using photochemical approaches, involves selection of linkers and masking groups that functions as orthogonal pairs, cleave efficiently and display fast kinetics when exposed to appropriate stimuli. Other factors, such as mild cleavage conditions, bio-orthogonal reagents, and limited use of reagents and inert by-products, shall govern the design and selection of photo-chemistries.

Examples of representative photocleavable linkers and masks are shown in Table 1. It should be noted that the chemistry of the linker is such that the linker has two attachments sites to allow binding to the targeting moiety as well as binding to the signal generator. The photo-active mask has one attachment point to the signal generator. Reported reaction times are based on reaction kinetics measured in water or polar solvents and were collected from the chemical literature.

TABLE 1

Examples of photocleavable linkers and mask

| Photocleavable linker | $\lambda$max (nm) | $\lambda$ (nm) Excitation Window (tail of absorption band)* | Time to Photocleave (mins) |
|---|---|---|---|
| o-nitrobenzyl | 260 | 360-405 | <5 |
| phenacyl | 250 | 300-340 | n/a |
| Nitropiperonyloxymethyl | 350 | 350-380 | n/a |
| Coumarin | 350 | 350-375 | 2 |
| 7-diethylaminocoumarin-4-yl)methyl | 370 | 390-410 | <1 |
| Quinolinyl benzene sulfonate | 275 | 315-330 | 10 |
| Anthraquinone | 250 | 340-380 | n/a |
| Benzoin | 245 | 300-350 | n/a |
| Dimethoxybenzoin | 310 | 320-360 | 5-7 |

*excitation at the tail of the photocleavable linker allows two or more orthogonal photocleavable linker choices based on the choosing a specific wavelength of light for cleaving and/or using band-pass filters.

In certain other embodiments, the linker and mask may be activated/deactivated through chemical means by the addition of a chemical agent. In a chemical approach chemically-cleavable groups may be used wherein the cleavage conditions involve the use of reagents that may include nucleophiles, electrophiles, acid, base, oxidizing or reducing agents. In certain embodiments, it is preferred that the reagent selected is such that it affords mild cleavage conditions, is bioorthogonal reagents, produces high cleavage yields at low concentrations of reagent, and is amenable to facile elimination of excess reagents and by-products.

In certain embodiments, a chemical agent may include one or more chemicals capable of modifying the signal generator or the cleavable linker between the signal generator and the binder. A chemical agent may be contacted with the signal generator in the form of a solid, a solution, a gel, or a suspension. Suitable chemical agents useful to modify the signal include agents that modify pH (for example, acids or bases), electron donors (e.g., nucleophiles), electron acceptors (e.g., electrophiles), oxidizing agents, reducing agents, or combinations thereof.

In some embodiments, a chemical agent may include a base, for example, sodium hydroxide, ammonium hydroxide, potassium carbonate, or sodium acetate. In some embodiments, a chemical agent may include an acid, for example, hydrochloric acid, sulfuric acid, acetic acid, formic acid, trifluoroacetic acid, or dichloroacetic acid. In some embodiments, a chemical agent may include nucleophiles, for example, cyanides, phosphines, or thiols. In some embodiments, a chemical gent may include reducing agents, for example, phosphines, thiols, sodium dithionite, or hydrides that can be used in the presence of water such as borohydride or cyanoborohydrides. In some embodiments, a chemical agent may include oxidizing agents, for example, active oxygen species, hydroxyl radicals, singlet oxygen, hydrogen peroxide, or ozone. In some embodiments, a chemical agent may include a fluoride, for example tetrabutylammonium fluoride, pyridine-HF, or $SiF_4$.

In certain embodiments, the chemical agent may be applied to the stained biological sample to modify the signal. In some embodiments, signal modification may include one or more changes in observed signal characteristics, for example, a decrease in observed signal intensity, a shift in the signal peak, a change in the resonant frequency, or removal of the signal generator as a result of cleavage from the binder. In some embodiments, modification of the signal may refer to a decrease in the signal intensity by an amount in a range of greater than about 50 percent. In some embodiments, modification of the signal may refer to a decrease in the signal intensity by an amount in a range of greater than about 60 percent. In some embodiments, modification of the signal may refer to a decrease in the signal intensity by an amount in a range of greater than about 80 percent. In some embodiments, modification of the signal may refer to a decrease in the signal intensity by an amount in a range of greater than about 95 percent.

In certain embodiments, it is preferable that the chemical agent essentially does not affect the integrity of the signal generator. Instead it is preferable that the chemical agent be capable of selectively cleaving one or more bonds present within the linker and the mask, rendering signal generators deactivated or activated respectfully. In certain embodiments, selection of the chemical agent may depend, in part, on the concentration of the signal generator, temperature, or pH of the sample.

Table 2 shows representative examples of chemically cleavable functionalities that can be employed as either linkers or masks. As described with reference to the photo-activatable links and masks; the chemistry of the linker is such that the linker has two attachments sites to allow binding to the targeting moiety as well as binding to the signal generator. The mask requires only one attachment point to the signal generator. Reaction times are estimates based on available data.

orthogonally cleavable linkers, signal generators, and masks that can be cleaved under a set of conditions that do not significantly affect the other cleavable linkers, signal generators and masks or the sample.

For example, to allow simultaneous association and subsequent imaging of targets in a biological sample; two sets of probes, having antibodies specific to each of the targets may be used. The first set would contain signal generators that have sufficient resolution to be detected. The set would be such that each antibody would be modified with the signal generator attached through a cleavable linker. The second set would utilize the same series of signal generators as the first, however in the second set, the signal generators would be masked. The cleavable linker of the first set are paired with the mask of the second set such that the linker and the mask are removed simultaneously. After application of the probes to the biological sample, imaging that occurs would be representative of the first set of probes. Applying conditions to the biological sample to effect cleavage, of the linker and mask, the first set of probes is deactivated while the masked probes are activated under the same conditions that are used to cleave the signals from the first set. The second series of probes, newly activated, may then be imaged.

In some embodiments cleavable linker and masks may be susceptible to different chemistries that are compatible with each other and can be used in combination in a single step. For example, the first set of signals may be attached to the first set of probes through a photocleavable linker and the masks masking the signals of second set of probes may be acid

TABLE 2

Examples of linker-mask pairs cleavable by various chemistries.

| Cleavage Stimuli | Cleavable Group | Examples | Ease of Cleavage (min) |
| --- | --- | --- | --- |
| Acidic reagents | P-methoxybenzyl, phosphoramidate, acetal, hydrazone, t-butylcarbamate, Trityl, substituted trityl (DMT) | DMT cleaved with mild acid (pH ~5) | 90 sec e.g., DMT |
| Basic reagents | Cyanoethylgroup, sulfone, hydrazone, acylhydrazone, acylhydrazone | N-alkylation acylsulfonamide cleave rapidly in minutes in $NaN_3$. | <2 |
| Reducing reagents | Disulfide bridges, azo compounds | Azo (5 mM $Na_2S_2O_4$, buffer, pH-7.4, RT); TCEP:$NH_4HCO_3$ (8:2) | <5 (azo) |

It is worth noting that the chemical/photochemical orthogonality of a linker-mask pair need only be verified toward the chemistries that precede it in the workflow and not for all the chemistries. For example, consider an embodiment wherein two photo-cleavable linkers are utilized in the first and second cycles of an imaging experiment and a chemically cleavable linker is employed during the third imaging cycle. The photo-cleavable linker utilized during the first imaging cycle need not be orthogonal to the photo or chemically cleavable linkers employed in the second or third imaging cycles. However, the photo-cleavable linker employed in the second step must be stable to the conditions required for cleavage of the first, and the chemically cleavable linker employed in the third step must be compatible with the conditions employed for cleavage of the linkers following the first and second imaging cycles.

In some embodiments, the method includes the steps of contacting a biological sample with a plurality of multiple sets of probes and physically binding the plurality of probes to a plurality of targets. The probes comprises a series of labile. In such an example, after imaging the first set of probes, the samples may be irradiated in an acidic medium to simultaneous remove first set of signals while activating the second set.

In certain embodiments the number of sets of probes can be increased as can the rounds of imaging needed to capture all the potential targets. The probes can be added simultaneous to the biological sample prior to any imaging step. In other embodiments, multiple sets of probes may be added to the biological sample with multiple rounds of imaging followed by addition of one or more sets of probes.

In some embodiments, the number of probes that can be used at a given time is dependent upon the method of detection and spectral resolution, whereby there is enough spectral separation of the dye to allow qualitative and/or quantitative analysis. As such, the invention increases the capacity of in situ multiplex analysis in a single round of probe staining which can then be multiplied by the number of repetitive rounds. Quantitative analysis by characterization by the strength and characteristics of the detected signal.

Table 3 shows a representative chart showing a selection of orthogonal linkers and masking agents for imaging a specific number of targets, wherein the probes comprise modified antibodies and wherein the antibodies are used to bind to targets present within a biological sample. Each set of linker and mask is cleaved by a chemistry that is orthogonal to the chemistry required to cleave sets of linkers and masks that precede it.

TABLE 3

Analysis of 12 probes comprising antibody as binders employing 3 signal generators and 4 imaging rounds

| Antibody | Conjugate | Cleavage | Imaging round |
|---|---|---|---|
| AB-1 | L1-SG1 | na | 1 |
| AB-2 | L1-SG2 | na | 1 |
| AB-3 | L1-SG3 | na | 1 |
| AB-4 | L2-SG1-M1 | L1-M1 | 2 |
| AB-5 | L2-SG2-M1 | L1-M1 | 2 |
| AB-6 | L2-SG3-M1 | L1-M1 | 2 |
| AB-7 | L3-SG1-M2 | L2-M2 | 3 |
| AB-8 | L3-SG2-M2 | L2-M2 | 3 |
| AB-9 | L3-SG3-M2 | L2-M2 | 3 |
| AB-10 | L4-SG1-M3 | L3-M3 | 4 |
| AB-11 | L4-SG2-M3 | L3-M3 | 4 |
| AB-12 | L4-SG3-M3 | L3-M3 | 4 |

As shown in Table 3, twelve antibodies labeled in the table as AB 1 through 12 may be selected for use as the binding component of probes for identifying specific targets. The twelve antibodies are associated with three signal generators (SG 1 through 3) such that during imaging after each round of signal removal and activation, the signal generators are distinctive with sufficient spectral resolution. The number of probes that may be simultaneously bound to the target may depend on the type of detection employed, that is, the spectral resolution achievable in each round. For example, for fluorescence-based signal generators, up to five different probes (providing up to five spectrally resolvable fluorescent signals) may be individually detected in accordance with the known methods, thereby increasing the number of probes that may be simultaneously bound to the targets to 20 probes detectable over four rounds of signal removal and activation using 3 orthogonally cleavable linker and mask sets. This number can be increased further by incorporating additional orthogonal chemistries to create additional linker and mask sets. Spectrally resolvable, in reference to a plurality of fluorescent signal generators, indicates that the fluorescent emission bands of the attached signal generators are sufficiently distinct, that is, sufficiently non-overlapping, such that, the antibody binders to which the respective signal generators are attached may be distinguished on the basis of the fluorescent signal generated by the respective signal generators using standard photodetection systems.

In some embodiments all probes may by simultaneously bound but may be sequentially detected in sets of 1-5 probes per cycle. As shown in Table 3, multiple imaging rounds occur (imaging rounds 1 through 4). In some embodiments, more than 5 probes may be used, based on spectral resolution.

As illustrated further in Table 3, a set number of linker and masking agent pairs are chosen which are capable of undergoing cleavage under the same conditions. These are depicted as linkers and masks 1 through 3, wherein the numeric designation represents a orthogonal pair (Table 3). The number of orthogonal pairs corresponds to one less that the number of imaging rounds to be performed. In certain embodiments, the probes comprise fluorescently labeled antibodies added together to a biological sample, either concurrently or in sequence, prior to imaging. The biological sample is then imaged. After the initial image, the first linker-mask pair is subjected to selective cleavage and the sample is washed to remove any residual material. This results in deactivation of the first series of antibody probes, and the activation of a subsequent series of signal generators. The biological sample may then be reimaged. The process is then repeated.

This process is shown schematically in FIG. 1 showing simultaneous and sequential analysis of the multiple biomarkers; 4 sets of three antibody probes analyzed in a total of four imaging rounds. As depicted in FIG. 1 this type of analysis has the advantage of reducing analysis time significantly as well as maintaining sample viability due to reduced handling and cycling protocols.

The same approach can be used with other types of probes such as probes comprising nucleic acid or lectin binders. The process may also be repeated numerous times, that is simultaneous incubation with dozen or more probes and sequential detection of small sets of targets by remove signal from an already imaged set and generating new signal from the next set to be imaged. After imaging of the last set in the example described in Table 3 and FIG. 1, linker 4 may be cleaved and a new set of 12 antibodies may be hybridized with same linker-mask pairs as the first set to detect an additional set of 12 targets.

The number of probes that may be simultaneously bound to the target may depend on the type of detection employed, that is, the spectral resolution achievable. For example, for fluorescence-based signal generators, up to five different probes (providing up to five spectrally resolvable fluorescent signals) may be employed in accordance with the disclosed methods. Spectrally resolvable, in reference to a plurality of fluorescent signal generators, indicates that the fluorescent emission bands of the signal generators are sufficiently distinct, that is, sufficiently non-overlapping, such that, binders to which the respective signal generators are attached may be distinguished on the basis of the fluorescent signal generated by the respective signal generators using standard photodetection systems. In some embodiments all probes may by simultaneously bound but the sequentially detected in sets of 1-5 probes per cycle. In some embodiments, more than 5 probes may be used, based on spectral resolution.

In certain embodiments the number of probes (P) that may be added prior to the first imaging round is dependent on the following formula:

$$P_x = SG_y * (OP_z + 1)$$

wherein x is the number of probes comprising a specific binder;

y is equal to the number of signal generators (SG); and z is equal to the number of orthogonal linker-mask pairs (OP).

In certain embodiments, x is an integer between 2 and 100, preferably and integer between 10 and 80 and more preferably an integer between 12 and 50. As such, in certain embodiments y is an integer between 2 and 20, more preferably and integer between 2 and 10 and most preferably and integer between 3 and 6. In certain embodiments z is an integer between 1 and 25, more preferable and integer between 2 and 10, and most preferable and integer between 2 and 5.

In certain embodiments the probe preferably comprises antibody based binders.

Figure 2A:
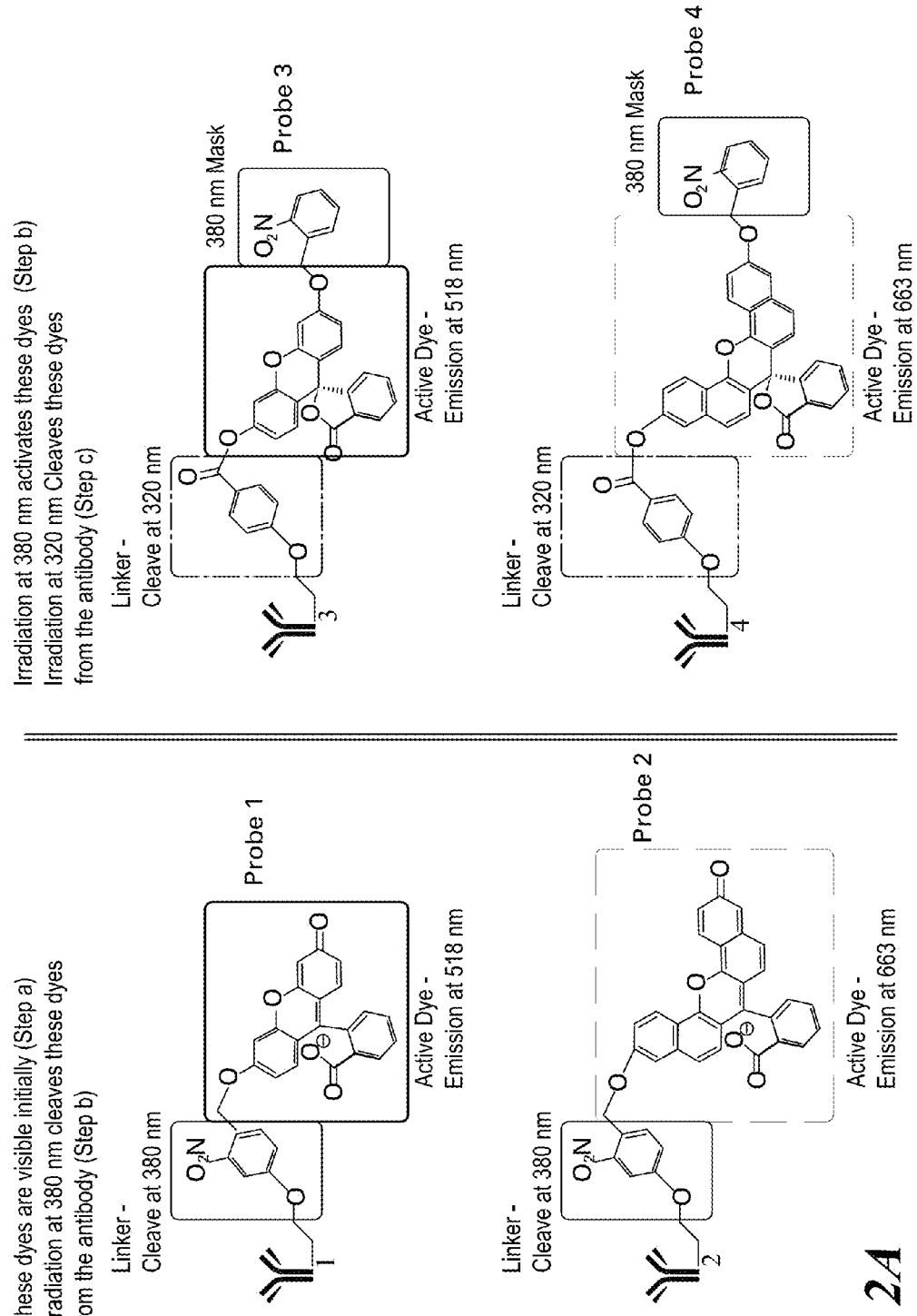
FIG. 2A is a schematic representative example of one embodiment wherein photo-induced cleavage is used; showing treatment steps a-c.
Figure 2B:
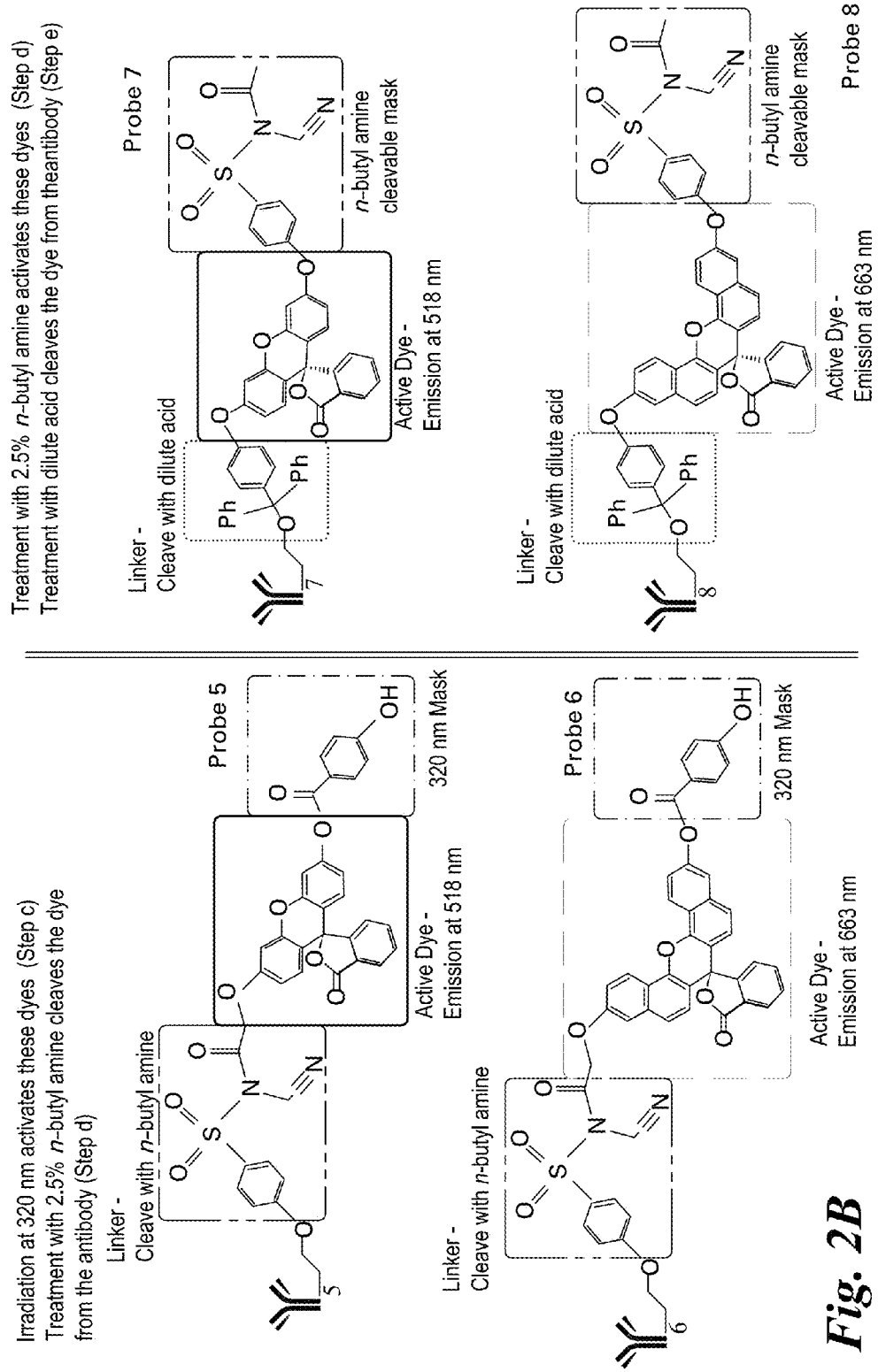
FIG. 2B is a schematic representative example of one embodiment wherein both photo-induced cleavage and a chemical agent are used; showing treatment steps c-e.
Figure 2C:
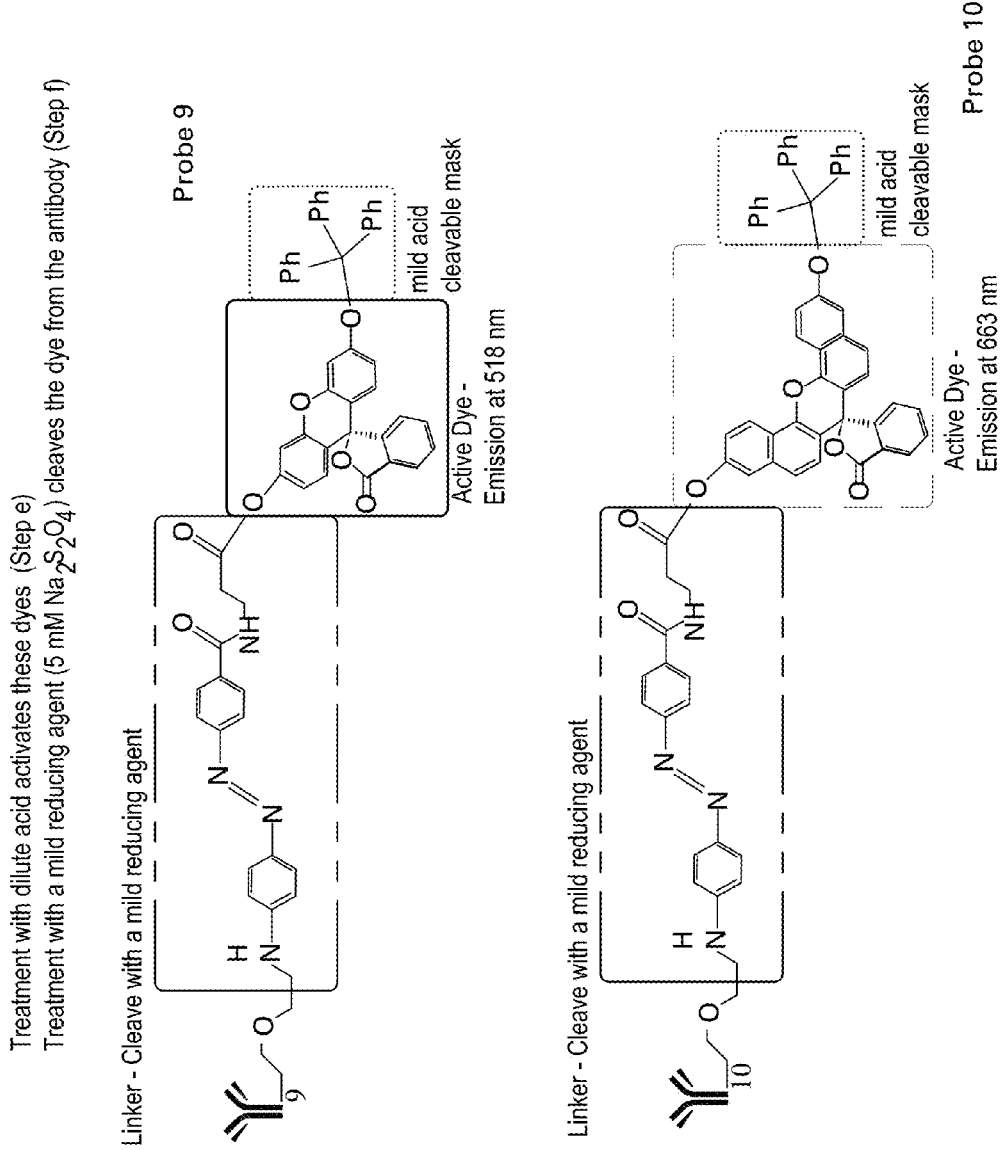
FIG. 2C is a schematic representative example of one embodiment wherein both photo-induced cleavage and a chemical agent are used; showing treatment steps e and f.

In certain embodiments the cleavable pairs comprise linker-mask pairs which are deactivated/activated using photo chemistry, a chemical agent or agents, or a combination thereof. FIGS. 2A-2C (steps a-f) is a representative example of one embodiment wherein both photochemical cleavage and chemical agents are used. As shown, 10 antibody probes are used along with two signal generators. A series of 4 linker-mask pairs are used such that all 10 antibody probes are detectable after initial imaging and 4 separate rounds of treatment and imaging. As shown, the 10 antibody conjugates may be added to the biological sample concurrently. As shown in FIG. 2A, only the initially active antibody conjugates would be visible by fluorescence at the outset (step a). It should be noted that the signal generators chosen emit in the tautomeric, non-cyclic form. Irradiation at 380 nm would silence the initial dyes, and unmask the second set (step b). Irradiation at 320 silences the second set and activates the third (step c). As shown in FIG. 2B, treatment with n-butylamine inactivates the third set while simultaneously activating the fourth (step d). Treatment with dilute acid inactivates the fourth set while activating the fifth (step e) (FIG. 2C). Treatment with a mild reducing agent would serve to inactivate the fifth dye set (step f). The use of additional dyes or chemically orthogonal linkers would expand the number of Ab-dye conjugates that could be visualized in a single pass. After removal of the fifth set another set of 10 probes using the same series of linker-mask pairs and same fluorphores may be used to detect 10 additional targets by repeating the process.

In certain embodiments, the method further includes detecting a first set of signals from the first set of the plurality of probes. The sample is irradiated in the presence of a reaction media, thereby initiating a photoreaction that modifies the first set of signals from the first set of the plurality of probes, as such deactivating the signals. The method further includes generating the second set of signals from the second set of the plurality of targets and detecting the second set of signals. The generation of the second set of signals may comprise activation and deactivation of signal-generating moieties e.g., by cleaving linkers and removing masking agents. In certain embodiments, this step of activation, deactivation is repeated with other sets (n-sets) of the plurality of probes.

In yet other embodiments, the method includes detecting a first set of signals from the first set of the plurality of probes. A chemical reagent is applied to the plurality of probes that modifies the first set of signals from the first set of the plurality of probes, as such deactivating the signals. The method further includes generating the second set of signals from the second set of the plurality of targets and detecting the second set of signals. The generation of the second set of signals may comprise activation and deactivation of signal-generating moieties e.g., by cleaving linkers and removing masking agents by way of a chemical agent. In certain embodiments, this step of activation, deactivation is repeated with other sets (n-sets) of the plurality of probes.

In yet another embodiment, the method includes using at least one electron transfer reagent and at least one chemical reagent for activation and deactivations. The electron transfer agent and chemical agent are used to facilitate the activation and deactivation of different orthogonal pairs. In certain cases, the electron transfer reagent as used allows for photo induced chemical bleaching (PICB). While PICB may not be as desirable in the cycling approach due to decrease selectivity and changes in other masked signals, it does has use depending on when it is used in the process. For example, in certain embodiments PICB may be used as the last deactivation step before repeating the process by hybridizing another set of binders.

A biological sample in accordance with one embodiment of the invention may be solid or fluid. Suitable examples of biological samples may include, but are not limited to, cultures, blood, plasma, serum, saliva, cerebral spinal fluid, pleural fluid, milk, lymph, sputum, semen, urine, stool, tears, saliva, needle aspirates, external sections of the skin, respiratory, intestinal, and genitourinary tracts, tumors, organs, cell cultures or cell culture constituents, or solid tissue sections. Cell cultures may include mixed cell culture, stem cell colonies or cultures derived from various cancer or primary cell lines. In some embodiments, the biological sample may be analyzed as is, that is, without harvest and/or isolation of the target of interest. In an alternative embodiment, harvesting and isolation of targets may be performed prior to analysis. In some embodiments, the methods disclosed herein may be particularly suitable for in vitro analysis of biological samples.

A biological sample may include any of the aforementioned samples regardless of their physical condition, such as, but not limited to, being frozen or stained or otherwise treated. In some embodiments, a biological sample may include compounds which are not naturally intermixed with the sample in nature such as preservatives, anticoagulants, buffers, fixatives, nutrients, antibiotics, or the like.

In some embodiments, a biological sample may include a tissue sample or section, a whole cell, a cell constituent, e.g., cell organelle, a cytospin, or a cell smear. In some embodiments, a biological sample essentially includes a tissue sample. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In some embodiments, a biological sample includes tissue sections from healthy or diseased tissue samples (e.g., tissue section from colon, breast tissue, and prostate). A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to at least two different targets (at morphological or molecular level). In some embodiments, tissue microarray may be used. In some embodiments, the same section of tissue sample may be analyzed with respect to at least four different targets (at morphological or molecular level). In some embodiments, the same section of tissue sample may be analyzed with respect to greater than four different targets (at morphological or molecular level). In some embodiments, the same section of tissue sample may be analyzed at both morphological and molecular levels.

A tissue section, if employed as a biological sample may have a thickness in a range that is less than about 100 micrometers, in a range that is less than about 50 micrometers, in a range that is less than about 25 micrometers, or in range that is less than about 10 micrometers.

In some embodiments, the biological sample may comprise one or more of proteins, carbohydrates or nucleic acids. In some embodiments, a biological sample or the targets in the biological sample may be adhered to a solid support. A solid support may include microarrays (e.g., DNA or RNA microarrays), gels, blots, glass slides, beads, or ELISA plates. In some embodiments, a biological sample or the targets in the biological sample may be adhered to a membrane selected from nylon, nitrocellulose, and polyvinylidene difluoride. In some embodiments, the solid support may include a plastic surface selected from polystyrene, polycarbonate, and polypropylene.

A target may be present on the surface of a biological sample (for example, an antigen on a surface of a tissue section) or present in the bulk of the sample (for example, an antibody in a buffer solution). In some embodiments, a target may not be inherently present on the surface of a biological sample and the biological sample may have to be processed to make the target available on the surface (e.g., antigen recovery, enzymatic digestion, epitope retrieval, or blocking). In some embodiments, the target may be present in a body fluid such as blood, blood plasma, serum, or urine. In some other embodiments, the target may be fixed in a tissue, either on a cell surface, or within a cell.

Suitability of targets to be analyzed may be determined by the type and nature of analysis required for the biological sample. In some embodiments, a target may provide information about the presence or absence of an analyte in the biological sample. In another embodiment, a target may provide information on a state of a biological sample. For example, if the biological sample includes a tissue sample, the methods disclosed herein may be used to detect targets that may help in comparing different types of cells or tissues, comparing different developmental stages, detecting the presence of a disease or abnormality, or determining the type of disease or abnormality.

Targets may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may essentially include proteins or nucleic acids. In other embodiments, multiple types of targets, e.g., nucleic acids, polysaccharides, lipids, enzymes, enzyme substrates, ligands, receptors, antigens or haptens may be detected and/or analyzed in the same biological sample in one or multiple cycles. One or more of the aforementioned targets may be characteristic of particular cells, while other targets may be associated with a particular disease or condition. In some embodiments, targets that may be detected and analyzed using the methods disclosed herein may include, but are not limited to, prognostic targets, hormone or hormone receptor targets, lymphoid targets, tumor targets, cell cycle associated targets, neural tissue and tumor targets, or cluster differentiation targets.

Suitable examples of prognostic targets may include enzymatic targets such as galactosyl transferase II, neuron specific enolase, proton ATPase-2, or acid phosphatase.

Suitable examples of hormone or hormone receptor targets may include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, or insulin receptor.

Suitable examples of lymphoid targets may include alpha-1-antichymotrypsin, alpha-1-antitrypsin, B cell target, bcl-2, bcl-6, B lymphocyte antigen 36 kD, BM1 (myeloid target), BM2 (myeloid target), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage target, muramidase (lysozyme), p80 anaplastic lymphoma kinase, plasma cell target, secretory leukocyte protease inhibitor, T cell antigen receptor (JOVI 1), T cell antigen receptor (JOVI 3), terminal deoxynucleotidyl transferase, or unclustered B cell target.

Suitable examples of tumor targets may include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma target (HMB45), mesothelia, metallothionein, microphthalmia transcription factor (MITF), Muc-1 core glycoprotein, Muc-1 glycoprotein, Muc-2 glycoprotein, Muc-5AC glycoprotein, Muc-6 glycoprotein, myeloperoxidase, Myf-3 (Rhabdomyo sarcoma target), Myf-4 (Rhabdomyosarcoma target), MyoD1 (Rhabdomyosarcoma target), myoglobin, nm23 protein, placental alkaline phosphatase, prealbumin, prostate specific antigen, prostatic acid phosphatase, prostatic inhibin peptide, PTEN, renal cell carcinoma target, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, or von Willebrand factor.

Suitable examples of cell cycle associated targets may include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mc1-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, or topoisomerase II beta.

Suitable examples of neural tissue and tumor targets may include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma target, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, or ubiquitin.

Suitable examples of cluster differentiation targets may include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

Other suitable prognostic targets may include centromere protein-F (CENP-F), giantin, involucrin, lamin A&C (XB 10), LAP-70, mucin, nuclear pore complex proteins, p180 lamellar body protein, ran, r, cathepsin D, Ps2 protein, Her2-neu, P53, S100, epithelial target antigen (EMA), TdT, MB2, MB3, PCNA, or Ki67.

The methods disclosed herein involve the use of binders that physically bind to the target in a specific manner. In some embodiments, a binder may bind to a target with sufficient specificity, that is, a binder may bind to a target with greater affinity than it does to any other molecule. In some embodiments, the binder may bind to other molecules, but the binding may be such that the non-specific binding may be at or near background levels. In some embodiments, the affinity of the binder for the target of interest may be in a range that is at least 2-fold, at least 5-fold, at least 10-fold, or more than its affinity for other molecules. In some embodiments, binders with the greatest differential affinity may be employed, although they may not be those with the greatest affinity for the target.

In some embodiments, binding between the target and the binder may be affected by physical binding. Physical binding may include binding effected using non-covalent interactions. Non-covalent interactions may include, but are not limited to, hydrophobic interactions, ionic interactions, or hydrogen-bond interactions. In some embodiments, the target and the binder may have areas on their surfaces or in cavities giving rise to specific recognition between the two resulting in physical binding. In some embodiments, a binder may bind to a biological target based on the reciprocal fit of a portion of their molecular shapes.

Binders and their corresponding targets may be considered as binding pairs, of which non-limiting examples include immune-type binding-pairs, such as, antigen/antibody, antigen/antibody fragment, or hapten/anti-hapten; nonimmune-type binding-pairs, such as biotin/avidin, biotin/streptavidin, folic acid/folate binding protein, hormone/hormone receptor, lectin/specific carbohydrate, enzyme/enzyme, enzyme/substrate, enzyme/substrate analog, enzyme/pseudo-substrate (substrate analogs that cannot be catalyzed by the enzymatic activity), enzyme/co-factor, enzyme/modulator, enzyme/inhibitor, or vitamin B12/intrinsic factor. Other suitable examples of binding pairs may include complementary nucleic acid fragments (including DNA sequences, RNA sequences, LNA sequences, and PNA sequences or other modified nucleic acids known in the literature); Protein A/antibody; Protein G/antibody; nucleic acid/nucleic acid binding protein; or polynucleotide/polynucleotide binding protein.

In some embodiments, the binder may be a sequence- or structure-specific binder, wherein the sequence or structure of a target recognized and bound by the binder may be sufficiently unique to that target.

In some embodiments, the binder may be structure-specific and may recognize a primary, secondary, or tertiary structure of a target. A primary structure of a target may include specification of its atomic composition and the chemical bonds connecting those atoms (including stereochemistry), for example, the type and nature of linear arrangement of amino acids in a protein. A secondary structure of a target may refer to the general three-dimensional form of segments of biomolecules, for example, for a protein a secondary structure may refer to the folding of the peptide "backbone" chain into various conformations that may result in distant amino acids being brought into proximity with each other. Suitable examples of secondary structures may include, but are not limited to, alpha helices, beta pleated sheets, or random coils. A tertiary structure of a target may be is its overall three dimensional structure. A quaternary structure of a target may be the structure formed by its noncovalent interaction with one or more other targets or macromolecules (such as protein interactions). An example of a quaternary structure may be the structure formed by the four-globin protein subunits to make hemoglobin. A binder in accordance with the embodiments of the invention may be specific for any of the aforementioned structures.

An example of a structure-specific binder may include a protein-specific molecule that may bind to a protein target. Examples of suitable protein-specific molecules may include antibodies and antibody fragments, nucleic acids (for example, aptamers that recognize protein targets), or protein substrates (non-catalyzable).

In some embodiments, a target may include an antigen and a binder may include an antibody. A suitable antibody may include monoclonal antibodies, polyclonal antibodies, multispecific antibodies (for example, bispecific antibodies), or antibody fragments so long as they bind specifically to a target antigen.

In preferred embodiments, the binder is an antibody that binds specifically to a target. The antibody is further coupled to a signal generator through a linking moiety and is specifically designed to be cleaved, under specific reaction conditions in a manner that allows both deactivation of the signal generator coupled to the linker and potential activation of a second signal generator bond to a masking agent.

In some embodiments, a biological sample may include a cell or a tissue sample and the methods disclosed herein may be employed in immunohistochemistry (IHC). Immunochemistry may involve binding of a target antigen to an antibody-based binder to provide information about the tissues or cells (for example, diseased versus normal cells). Examples of antibodies (and the corresponding diseases/disease cells) suitable as binders for methods disclosed herein include, but are not limited to, anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oncoprotein (p21) antibody, anti-Lewis X (also called CD15)

antibody, anti-Ki-67 antibody (cellular proliferation), anti-PCNA (multiple cancers) antibody, anti-CD 3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblastic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD 41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salivary, glial cells), anti-tau antigen antibody (Alzheimer's disease), anti-fibrin antibody (epithelial cells), anti-keratins antibody, anti-cytokeratin antibody (tumor), anti-alpha-catenin (cell membrane), or anti-Tn-antigen antibody (colon carcinoma, adenocarcinomas, and pancreatic cancer).

Other specific examples of suitable antibodies may include, but are not limited to, anti-proliferating cell nuclear antigen, clone pc10 (Sigma Aldrich, P8825); anti smooth muscle alpha actin (SmA), clone 1A4 (Sigma, A2547); rabbit anti beta catenin (Sigma, C 2206); mouse anti pan cytokeratin, clone PCK-26 (Sigma, C1801); mouse anti estrogen receptor alpha, clone 1D5 (DAKO, M 7047); beta catenin antibody, clone 15B8 (Sigma, C 7738); goat anti vimentin (Sigma, V4630); cycle androgen receptor clone AR441 (DAKO, M3562); Von Willebrand Factor 7, keratin 5, keratin 8/18, e-cadherin, Her2/neu, Estrogen receptor, p53, progesterone receptor, beta catenin; donkey anti-mouse (Jackson Immunoresearch, 715-166-150); or donkey anti rabbit (Jackson Immunoresearch, 711-166-152).

Regardless of the type of binder and the target, the specificity of binding between the binder and the target may also be affected depending on the binding conditions. Suitable binding conditions may be realized by modulation one or more of pH, temperature, or salt concentration.

The type of signal generator suitable for the methods disclosed herein may depend on a variety of factors, including the nature of the analysis being conducted, the type of the energy source and detector used, the type of electron transfer reagent employed, the type of binder, and/or the type of target.

A suitable signal generator may include a molecule or a compound capable of providing a detectable signal. A signal generator may provide a characteristic signal following interaction with an energy source or a current. An energy source may include electromagnetic radiation source and a fluorescence excitation source. Electromagnetic radiation source may be capable of providing electromagnetic energy of any wavelength including visible, infrared and ultraviolet. Electromagnetic radiation may be in the form of a direct light source or may be emitted by a light emissive compound such as a donor fluorophore. A fluorescence excitation source may be capable of making a source fluoresce or may give rise to photonic emissions (that is, electromagnetic radiation, directed electric field, temperature, physical contact, or mechanical disruption). Suitable signal generators may provide a signal capable of being detected by a variety of methods including optical measurements (for example, fluorescence), electrical conductivity, or radioactivity. Suitable signal generators may be, for example, light emitting, energy accepting, fluorescing, radioactive, or quenching.

A suitable signal generator may be sterically and chemically compatible with the constituents to which it is bound, for example, a binder. Additionally, a suitable signal generator may not interfere with the binding of the binder to the target, nor may it significantly affect the binding specificity of the binder. A suitable signal generator may be organic or inorganic in nature. In some embodiments, a signal generator may be of a chemical, peptide or nucleic acid nature.

A suitable signal generator may be directly detectable. A directly detectable moiety may be one that may be detected directly by its ability to emit a signal, such as for example a fluorescent label that emits light of a particular wavelength following excitation by light of another lower, characteristic wavelength and/or absorb light of a particular wavelength.

A signal generator, suitable in accordance with the methods disclosed herein may be amenable to manipulation on application of an electron transfer reagent. In some embodiments, a signal generator may be capable of being bleached, e.g., the signal it generates may be diminished or destroyed as result of the signal generator being modified in the course of a photoreaction. Chemical modification may include complete disintegration of the signal generator or modification of the signal-generating component of the signal generator. In some embodiments, the signal generator is charged.

Modification of the signal-generating component may include any chemical modification (such as addition, substitution, or removal) that may result in the modification of the signal generating properties. For example, cleaving a conjugated signal generator may result in destruction of chromogenic properties of the signal generator. Similarly, substitution of a fluorescence-inhibiting functional group on a fluorescent signal generator may result in modification of its fluorescent properties. In some embodiments, one or more signal generators substantially resistant to inactivation by a specific chemical agent may be used as a control probe in the provided methods.

In some embodiments, a signal generator may be selected from a light emissive molecule, a radioisotope (e.g., P32 or H3, 14C, 125I and 131I), an optical or electron density marker, a Raman-active tag, an electron spin resonance molecule (such as for example nitroxyl radicals), an electrical charge transferring molecule (i.e., an electrical charge transducing molecule), a semiconductor nanocrystal, a semiconductor nanoparticle, a colloid gold nanocrystal, a microbead, a magnetic bead, a paramagnetic particle. It is noted that some of these signal generators may not be used in a quenched form, as such a radioisotope signal generator is more applicable to use in the first detection cycle.

In some embodiments, a signal generator may be an optical signal generator, e.g., may include a light-emissive molecule.

A light emissive molecule may emit light in response to irradiation with light of a particular wavelength. Light emissive molecules may be capable of absorbing and emitting light through luminescence (non-thermal emission of electromagnetic radiation by a material upon excitation), phosphorescence (delayed luminescence as a result of the absorption of radiation), chemiluminescence (luminescence due to a chemical reaction), fluorescence, or polarized fluorescence. Non-limiting examples of optical signal generators include a fluorescent signal generator, e.g., a fluorophore, a Raman-active tag or a chromophore.

In some embodiments, a signal generator may essentially include a fluorophore. In some embodiments, a signal generator may essentially include a fluorophore attached to an antibody, for example, in an immunohistochemistry analysis. Suitable fluorophores that may be conjugated to a primary antibody include, but are not limited to, Fluorescein, Rhodamine, Texas Red, VECTOR Red, ELF (Enzyme-Labeled Fluorescence), Cy2, Cy3, Cy3.5, Cy5, Cy7, Fluor X, Calcein, Calcein-AM, CRYPTOFLUOR, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl) amino]caproyl] (NBD), BODIPY, boron dipyrromethene difluoride, 1,3-dichloro-7-hydroxy-9,9-dimethyl-2(9H)-Acridinone (DDAO), dimethylacridinone (DAO), Oregon Green, MITOTRACKER Red, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, Infra-Red (IR) Dyes, Cyclic GDP-Ribose (cGDPR), Calcofluor White, Lissamine, Umbelliferone, Tyrosine or Tryptophan. In some embodiments, the fluorophore can be cyanine, rhodamine, coumarins or pyrelium dyes. In some embodiments, a signal generator may essentially include a xanthene dye. In some embodiments, a signal generator may essentially include a cyanine dye. In further embodiments, a signal generator may essentially include one or more a Cy2 dye, a Cy3 dye, a Cy5 dye, or a Cy7 dye. In alternative embodiments, the signal generator may be BODIPY, rhodamine, 1,3-dichloro-7-hydroxy-9,9-dimethyl-2(9H)-Acridinone (DDAO) or 7-hydroxy-9,9-dimethyl-2(9H)-Acridinone (DAO).

In some embodiments, the signal generator may be part of a FRET pair. FRET pair includes two fluorophores that are capable of undergoing FRET to produce or eliminate a detectable signal when positioned in proximity to one another. Some examples of donors may include Alexa 488, Alexa 546, BODIPY 493, Oyster 556, Fluor (FAM), Cy3, or TTR (Tamra). Some examples of acceptors may include Cy5, Alexa 594, Alexa 647, or Oyster 656.

As described hereinabove, one or more of the aforementioned molecules may be used as a signal generator. In some embodiments, one or more of the signal generators may be amenable to signal destruction and the signal generator may essentially include a molecule capable of being bleached by photoinduced chemical bleaching (PICB). In some embodiments, a signal generator may include a fluorophore capable of being chemically modified in a photoreaction that also involves an electron transfer reagent and irradiation. In some embodiments, a signal generator may essentially include cyanine, BODIPY, rhodamine, or acridinone (e.g., DDAO and DAO), that can be modified in a photoreaction that also involves addition of an electron transfer reagent and irradiation. In some embodiments, a signal generator may include one or more a Cy2 dye, a Cy3 dye, a Cy5 dye, or a Cy7 dye that can be bleached by photoactivated chemical bleaching.

An electron transfer reagent may include one or more chemicals that can engage in a photoreaction with a molecule capable of undergoing photoexcitation. The molecule capable of undergoing photoexcitation may be a signal generator. An electron transfer reagent may be contacted with the sample in the form of a solid, a solution, a gel, or a suspension. In some embodiments, an electron transfer reagent may include a borate salt as more fully described in U.S. application Ser. No. 12/336,409 entitled 'Photoactivated Chemical Bleaching of Dyes' filed Dec. 11, 2011 incorporated herein by reference.

Other suitable electron transfer reagents may include sulfinates, enolates, carboxylates (e.g., ascorbic acid), organometallics and amines (e.g., triethanolamine, and N-phenylglycine). These and other electron transfer reagents have been previously described (see, e.g., Macromolecules 1974, 7, 179-187; Photogr. Sci. Eng. 1979, 23, 150-154; Topics in Current Chemistry, Mattay, J., Ed.; Springer-Verlag: Berlin, 1990, Vol. 156, pp 199-225; and Pure Appl. Chem. 1984, 56, 1191-1202.)

An electron transfer reagent to be used for photoactivated chemical bleaching is chosen such that the photoreaction between the electron transfer reagent and a signal generator is energetically favorable. In some embodiments, the electron transfer reagent and the photoexcited signal generator form an electron donor/acceptor pair, wherein an electron transfer from the electron transfer reagent to the signal generator is energetically favorable. The electron transfer may further lead to chemical modification of the signal generator, resulting in bleaching of the signal generator. Examples of electron transfer reagents and signal generators that can form electron donor/acceptor pairs include triaryl alkyl borates, such as triphenyl butyl borate as an electron transfer reagent and cyanine dyes (e.g., Cy3 and Cy5), BODIPY, rhodamine or acridone dyes as signal generators.

In some embodiments, where two or more signal generators may be employed simultaneously, a photoreaction may be capable of selectively modifying one or more signal generators. This selectivity may be derived from selective photoexcitation of the signal generator by irradiation at specific wavelength. The irradiation wavelength is chosen such that one or more signal generator may photoexcited, while the remaining one or more signal generator that may be present in a sample may remain unaffected. In some embodiments, irradiation limited to a range of wavelengths between 520-580 nm can be used for selective photoexciation of a Cy3 dye. In other embodiments, irradiation limited to a range of wavelengths between 620-680 nm can be used for selective photoexcitation of a Cy5 dye. In alternative embodiments, selective photoexcitation may be accomplished by using a laser.

The propensity of photoexcited signal generators to further undergo photoreaction may depend on the choice of the electron transfer reagent, as discussed above, as well as on the reaction conditions, such as temperature, solvent and pH.

In some embodiments, the activated/deactivation of the orthogonal pair occurs through photocleavage which is carried out at a temperature of 4-50° C., more preferably, at a temperature of 20-30° C.

In some embodiments, the activation/deactivation by photocleavage is carried out in a solution. In some embodiments, the solution is a buffered solution. In a further embodiment, the buffered solution is the solution buffered in phosphate buffered saline (PBS). In some embodiments, the solution is buffered at pH of 5-9. In a preferred embodiment, the pH of the solution is 6-8.

A biological sample may be contacted with one or more probes to bind the probes to a target in the biological sample.

In some embodiments, a target may not be easily accessible for binding with the probes and a biological sample may be further processed to facilitate the binding between the target and the binder in the probes, for example through antigen recovery, enzymatic digestion, epitope retrieval, or blocking.

Depending on the nature of the binder, the target, and the binding between the two, sufficient contact time may be allowed. In some embodiments, an excess of probe molecules (and accordingly binder molecules) may be employed to ensure all the targets in the biological sample are bound. After a sufficient time has been provided for the binding action, the sample may be contacted with a wash solution (for example, an appropriate buffer solution) to wash away any unbound probes. Depending on the concentration and type of probes used, a biological sample may be subjected to a number of washing steps with the same or different washing solutions being employed in each step.

The plurality of probes may be capable of binding different targets in the biological sample. For example, a biological sample may include two targets: target1 and target2 and two sets of probes may be used in this instance: probe1 (having binder1 capable of binding to target1) and probe2 (having binder2 capable of binding to target2). The plurality of probes may also comprise a plurality of multiple sets of target-binding probes. A plurality of probes may be contacted with the biological sample simultaneously (for example, as a single mixture) or sequentially (for example, a probe1 or probe set 1 may be contacted with the biological sample, followed by washing step to remove any unbound probe1, followed by contacting a probe2 or probe set 2 with the biological sample, and so forth). For example, the probe 1 or probe set 1 may comprise one or more antibody probes and probe 2 or probe set 2 may comprise FISH probes.

In some embodiments, a biological sample may include a whole cell, a tissue sample, or the biological sample may be adhered to a microarray, a gel, or a membrane. In some embodiments, a biological sample may include a tissue sample. The tissue sample may be obtained by a variety of procedures including, but not limited to surgical excision, aspiration or biopsy. The tissue may be fresh or frozen. In some embodiments, the tissue sample may be fixed and embedded in paraffin. The tissue sample may be fixed or otherwise preserved by conventional methodology; the choice of a fixative may be determined by the purpose for which the tissue is to be histologically stained or otherwise analyzed. The length of fixation may depend upon the size of the tissue sample and the fixative used. For example, neutral buffered formalin, Bouin's or paraformaldehyde may be used to fix or preserve a tissue sample.

In some embodiments, the tissue sample may be first fixed and then dehydrated through an ascending series of alcohols, infiltrated and embedded with paraffin or other sectioning media so that the tissue sample may be sectioned. In an alternative embodiment, a tissue sample may be sectioned and subsequently fixed. In some embodiments, the tissue sample may be embedded and processed in paraffin. Examples of paraffin that may be used include, but are not limited to, Paraplast, Broloid, and Tissuemay. Once the tissue sample is embedded, the sample may be sectioned by a microtome into sections that may have a thickness in a range of from about three microns to about five microns. Once sectioned, the sections may be attached to slides using adhesives. Examples of slide adhesives may include, but are not limited to, silane, gelatin, poly-L-lysine. In embodiments, if paraffin is used as the embedding material, the tissue sections may be deparaffinized and rehydrated in water. The tissue sections may be deparaffinized, for example, by using organic agents (such as, xylenes or gradually descending series of alcohols).

In some embodiments, aside from the sample preparation procedures discussed above, the tissue section may be subjected to further treatment prior to, during, or following immunohistochemistry. For example, in some embodiments, the tissue section may be subjected to epitope retrieval methods, such as, heating of the tissue sample in citrate buffer or Tris buffer or both in a sequential manner. In some embodiments, a tissue section may be optionally subjected to a blocking step to minimize any non-specific binding.

In some embodiments, the biological sample or a portion of the biological sample, or targets present in the biological sample may be adhered on the surface, e.g. DNA microarrays, or protein microarrays, or on the surface of solid supports (such as gels, blots, glass slides, beads, or ELISA plates). In some embodiments, targets present in the biological sample may be adhered on the surface of solid supports. Targets in the biological sample may be adhered on the solid support by physical bond formation, by covalent bond formation, or both.

In some embodiments, the targets in the biological sample may be adhered to membranes and probed sequentially using the methods disclosed herein. In some embodiments, targets in the biological sample may be processed before contacting the sample with the membrane. For example, embodiments involving methods for probing protein targets in a tissue sample may include the step of extracting the target proteins a biological sample of tissue homogenate or an extract. Solid tissues or whole cells may be first broken down mechanically using a blender (for larger sample volumes), using a homogenizer (smaller volumes), or by sonication. Different cell compartments and organelles may be separated using filtration and centrifugation techniques. Detergents, salts, and buffers may also be employed to encourage lysis of cells and to solubilize proteins. Similarly, embodiments involving methods for probing nucleic acids may include the step of preparing DNA or RNA fragments, for example using restriction endonucleases (for DNA).

In some embodiments, targets extracted from the biological sample may be further separated by gel electrophoresis. Separation of targets may be by isoelectric point (pI), molecular weight, electric charge, or a combination of these factors. The nature of the separation may depend on the treatment of the sample and the nature of the gel. A suitable gel may be selected from a polyacrylamide gel, an SDS-polyacrylamide gel, or an agarose gel.

A suitable membrane may be selected such that the membrane has non-specific target binding properties. In some embodiments, a suitable membrane may be selected from a polyvinylidene fluoride membrane, a nitrocellulose membrane, or a nylon membrane. In some embodiment, a suitable membrane may be selected such that the membrane may be substantially stable to multiple probing. In embodiments involving probing of targets using protein probes, the membranes may be blocked using a blocking solution to prevent non-specific binding of protein probes to the membranes. In embodiments, involving probing of DNA fragments, the DNA gel may be treated with a dilute HCl solution or an alkaline solution to facilitate more efficient transfer of the DNA from the gel to the membrane.

In some embodiments, the membrane may be subjected to temperatures in a range of about 60° C. to about 100° C. to covalently bind the targets to the membrane, for example DNA targets to a nitrocellulose membrane. In some embodiments, the membrane may be exposed to ultraviolet radiation to covalently bind the targets to the membrane, for example DNA targets to a nylon membrane. In some embodiments, the targets in the biological sample may not be separated by electrophoresis before blotting on a membrane and may be probed directly on a membrane, for example, in dot blot techniques.

A signal from the signal generator may be detected using a detection system. The nature of the detection system used may depend upon the nature of the signal generators used. The detection system may include an, a charge coupled device (CCD) detection system a fluorescent detection system, an electrical detection system, a photographic film detection system, a chemiluminescent detection system, an enzyme detection system, an optical detection system, a near field detection system, or a total internal reflection (TIR) detection system.

One or more of the aforementioned techniques may be used to observe one or more characteristics of a signal from a signal generator (coupled with a binder or coupled with an enzyme substrate). In some embodiments, signal intensity, signal wavelength, signal location, signal frequency, or signal shift may be determined using one or more of the aforementioned techniques. In some embodiments, one or more aforementioned characteristics of the signal may be detected, measured, and recorded.

In some embodiments, the detected signal is a fluorescent signal, and a probe bound to a target in a biological sample may include a signal generator that is a fluorophore. In some embodiments, the fluorescent signal may be measured by determining fluorescence wavelength or fluorescent intensity using a fluorescence detection system. In some embodiments, a signal may be detected in situ, that is, a signal may be detected directly from the signal generator associated through the binder to the target in the biological sample. In some embodiments, a signal from the signal generator may be analyzed within the biological sample, obviating the need for separate array-based detection systems.

In some embodiments, detecting, which may also be referred to as observing a signal, may include capturing an image of the biological sample. In some embodiments, a microscope connected to an imaging device may be used as a detection system, in accordance with the methods disclosed herein. In some embodiments, a signal generator (such as, fluorophore) may be excited and the signal (such as, fluorescence signal) obtained may be detected and recorded in the form of a digital signal (for example, a digitalized image). The same procedure may be repeated for different signal generators (if present) that are bound in the sample using the appropriate fluorescence filters.

In some embodiments, multiple different types of signals may be detected in the same sample. For example, one target may be detected with a fluorescent probe and a second target in the same sample may be detected with a chromogenic probe.

To modify the signal, a chemical agent may be applied to the sample. In some embodiments, signal modification may include a change in one or more signal characteristics, for example, a decrease or increase in intensity of signal, a shift in the signal peak, or a change in the resonant frequency. In some embodiments, a chemical reaction may modify the signal by substantially activating/deactivating, i.e., bleaching, the fluorescent signal generator and mask removal from another signal generator.

In some embodiments, a characteristic of the signal may be detected after the chemical agent or photobleaching to determine the effectiveness of the signal modification. For example, a color may be detected before the application of the agent and the color may be absent after the application while another color may be detected. In another example, fluorescence intensity from a fluorescent signal generator may be detected before the photoreaction and after the photoreaction. In some embodiments, a decrease or increase in signal intensity by a predetermined amount may be referred to as signal modification. In some embodiments, modification of the signal may refer to a change in the signal intensity by an amount in a range of greater than about 50 percent. In reference to an orthogonal pair one signal generator signal will be increased while the other decreased. In some embodiments wherein same signal generators are used to detect multiple sets of probes by cleaving the active signal generator from the first set while activating the masked signal from second set, no change in net intensity may be observed. In such cases samples will be exposed to cleavage and unmasking reagents for a predetermined set of time, determined previously for each linker and mask. In some embodiments, modification of the signal may refer to a change in the signal intensity by an amount in a range of greater than about 60 percent. In some embodiments, modification of the signal may refer to a change in the signal intensity by an amount in a range of greater than about 80 percent. In some embodiments, modification of the signal may refer to a change in the signal intensity by an amount in a range of greater than about 90 percent. In some embodiments, modification of the signal may refer to a change in the signal intensity by an amount in a range of greater than about 95 percent. In some embodiments, modification of the signal may refer to a change in the signal intensity by an amount in a range of about 100 percent, or to complete bleaching or activation from no prior detection.

In some embodiments, after contacting the sample with a subsequent (e.g., second, third, etc.) probe sets, deactivation and activation of the signal generator in a photoreaction or chemical reaction, and subsequent probe administration signal generation from already bound probes may be repeated multiple times. The binding, detecting, and bleaching steps may be repeated iteratively multiple times using an nth probe sets capable of binding to additional targets to provide the user with information about a variety of targets using a variety of probes and/or signal generators.

In some embodiments, binding, reacting (if applicable), orthogonal cleaving, and detecting steps may be repeated one or more times. In some embodiments the steps may be repeated at least 2, at least 5, at least 15, at least 30, at least 60 times, at least 100 times, or at least 150 times. In some embodiments, the series of steps may be repeated 25-30 times. In other embodiments, the series of steps may be repeated 2-10 times.

In still other embodiments, the cleaving and detecting steps may be repeated after an initial binding step such limiting the cleaving and detecting step to a single cycle. In still other embodiments, after multiple cleaving and detecting steps, the last set of signals may be cleaved or bleached and the sample may be subjected to a second round of staining with a series of orthogonally cleavable linkers, signal generators, and masks.

In some embodiments, a biological sample may include a cell or a tissue, and the sample may be contacted with a morphological stain before, during, or after the contacting step with the first set of probes or subsequent sets of probes. A morphological stain may include a dye that may stain different cellular components, in order to facilitate identification of cell type or disease status. In some embodiments, the morphological stain may be readily distinguishable from the signal generators in the probes, that is, the stain may not emit signal that may overlap with signal from the probe. For example, for a fluorescent morphological stain, the signal from the morphological stain may not autofluoresce in the same wavelength as the fluorophores used in the probes.

A morphological stain may be contacted with the biological sample before, during, or after, any one of the aforementioned steps. In some embodiments, a morphological stain may be contacted with biological sample along with the first probe contact step. In some embodiments, a morphological stain may be contacted with the biological sample before contacting the sample with an electron transfer reagent and irradiated after binding the first probe to the target. In some embodiments, a morphological stain may be contacted with a biological sample after contacting the sample with an electron transfer reagent and irradiation to modify the signal. In some embodiments, a morphological stain may be contacted with a biological sample along with the second probe contact step. In some embodiments, a biological sample may be contacted with the morphological stain after binding the second probe to the target. In some embodiments, where the morphological stains may result in background noise for the fluorescent signal from the signal generator, the morphological stains may be contacted with the biological sample after the probing, bleaching and repeated probing steps. For example, morphological stains like H&E may be sequentially imaged and registered after the methods disclosed herein.

In some embodiments, chromophores, fluorophores, or enzyme/enzyme substrates may be used as morphological stains. Suitable examples of chromophores that may be used as morphological stains (and their target cells, subcellular compartments, or cellular components) may include, but are not limited to, Hematoxylin (nucleic acids), Orange G (red blood, pancreas, and pituitary cells), Light Green SF (collagen), Romanowsky-Giemsa (overall cell morphology), May-Grunwald (blood cells), Blue Counterstain (Trevigen), Ethyl Green (CAS) (amyloid), Feulgen-Naphthol Yellow S (DNA), Giemsa (differentially stains various cellular compartments), Methyl Green (amyloid), pyronin (nucleic acids), Naphthol-Yellow (red blood cells), Neutral Red (nuclei), Papanicolaou stain (a mixture of Hematoxylin, Orange G and Bismarck Brown mixture (overall cell morphology)), Red Counterstain B (Trevigen), Red Counterstain C (Trevigen), Sirius Red (amyloid), Feulgen reagent (pararosanilin) (DNA), Gallocyanin chrom-alum (DNA), Gallocyanin chrom-alum and Naphthol Yellow S (DNA), Methyl Green-Pyronin Y (DNA), Thionin-Feulgen reagent (DNA), Acridine Orange (DNA), Methylene Blue (RNA and DNA), Toluidine Blue (RNA and DNA), Alcian blue (carbohydrates), Ruthenium Red (carbohydrates), Sudan Black (lipids), Sudan IV (lipids), Oil Red-O (lipids), Van Gieson's trichrome stain (acid fuchsin and picric acid mixture) (muscle cells), Masson trichrome stain (hematoxylin, acid fuchsin, and Light Green mixture) (stains collagen, cytoplasm, nucleioli differently), Aldehyde Fuchsin (elastin fibers), or Weigert stain (differentiates reticular and collagenous fibers).

Examples of suitable fluorescent morphological stains (and their target cells, subcellular compartments, or cellular components if applicable) may include, but are not limited to: 4',6-diamidino-2-phenylindole (DAPI) (nucleic acids), Hoechst 33258 and Hoechst 33342 (two bisbenzimides) (nucleic acids), Propidium Iodide (nucleic acids), Spectrum Orange (nucleic acids), Spectrum Green (nucleic acids), Quinacrine (nucleic acids), Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein, such as histones, ACMA, Quinacrine and Acridine Orange.

Examples of suitable enzymes (and their primary cellular locations or activities) may include, but are not limited to, ATPases (muscle fibers), succinate dehydrogenases (mitochondria), cytochrome c oxidases (mitochondria), phosphorylases (mitochondria), phosphofructokinases (mitochondria), acetyl cholinesterases (nerve cells), lactases (small intestine), acid phosphatases (lysosomes), leucine aminopeptidases (liver cells), dehydrogenases (mitochondria), myodenylate deaminases (muscle cells), NADH diaphorases (erythrocytes), and sucrases (small intestine).

In some embodiments, a morphological stain may be stable towards photo and or chemical cleavage and unmasking processes, that is, the signal generating properties of the morphological stain may not be substantially affected by a photo or chemical process. In some embodiments, where a biological sample may be stained with a probe and a morphological stain at the same time, a removal of the signal from the probe may not modify the signal from the morphological stain. In some embodiments, a morphological stain may be used as a control to co-register the molecular information (obtained through the iterative probing steps) and the morphological information (obtained through the morphological stains).

In some embodiments, the detecting steps include co-localizing at least two targets in the sample. Methods for co-localizing targets in a sample are described in U.S. patent application Ser. No. 11/686,649, entitled "System and Methods for Analyzing Images of Tissue Samples", filed on Mar. 15, 2007; U.S. patent application Ser. No. 11/500,028, entitled "System and Method for Co-Registering Multi-Channel Images of a Tissue Micro Array", filed on Aug. 7, 2006; U.S. patent application Ser. No. 11/606,582, entitled "System and Methods for Scoring Images of a Tissue Micro Array", filed on Nov. 30, 2006, and U.S. application Ser. No. 11/680,063, entitled Automated Segmentation of Image Structures, filed on Feb. 28, 2007, now U.S. Pat. No. 8,036,462, issued on Oct. 11, 2011, each of which is herein incorporated by reference.

In some embodiments, a location of the signal in the biological sample may be detected. In some embodiments, a localization of the signal in the biological signal may be detected using morphological stains. In some embodiments relative locations of two or more signals may be detected. A location of the signal may be correlated to a location of the target in the biological sample, providing information regarding localization of different targets in the biological sample. In some embodiments, an intensity value of the signal and a location of the signal may be correlated to obtain information regarding localization of different targets in the biological sample. For examples certain targets may be expressed more in the cytoplasm relative to the nucleus, or vice versa. In some embodiments, information regarding relative localization of targets may be obtained by comparing location and intensity values of two or more signals.

In embodiments employing blotting techniques, the detecting steps may include detecting a location of the signal on the blot. The location of the signal in the blot may be then correlated with calibration standards loaded along with the sample in the gel to obtain information regarding the molecular weight of the targets in the different bands. In some embodiments, a location of the signal on the blot may be correlated to a molecular weight of the target and the isoelectric point of the target, e.g., in 2D-PAGE. In some embodiments, structural proteins such as actin or tubulin may be probed using control probes in western blots to quantify the amount of targets in the sample.

In some embodiments, one or more of the detecting or correlating step may be performed using computer-aided means. In embodiments where the signal(s) from the signal generator may be stored in the form of digital image(s), computer-aided analysis of the image(s) may be conducted. In some embodiments, images (e.g., signals from the probe(s) and morphological stains) may be overlaid using computer-aided superimposition to obtain complete information of the biological sample, for example topological and correlation information.

In some embodiments, one or more of the aforementioned may be automated and may be performed using automated systems. In some embodiments, all the steps may be performed using automated systems.

The methods disclosed herein may find applications in analytic, diagnostic, and therapeutic applications in biology and in medicine. In some embodiments, the methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biological sample.

EXAMPLES

The following examples are intended only to illustrate methods and embodiments in accordance with the invention, and as such should not be construed as imposing limitations upon the claims.

Example 1

Synthesis of Dyes with Photocleavable Linkers (Dye-PC)

NHS ester of a masked (e.g. CMNB-caged carboxyfluorescein-NHS ester) or unmasked dye (carboxyfluorescein NHS ester) is conjugated to 1-[5-(aminomethyl)-2-nitrophenyl]ethanol in anhydrous dimethylformamide containing ~4 equivalents (excess) of N-methylmorpholine or N-ethyl-diisopropylamine. Product is purified by liquid chromatography and concentrated to dryness to give pure (>90%) Dye-PC.

Activation of Dye-PC

N,N'-Disuccinimidyl carbonate and triethylamine (2 eq) are added to a solution of Dye-PC (0.7 equivalent) in anhydrous acetonitrile or DMF. Reaction mixture is stirred at room temperature and followed by HPLC. After completion, solvent is removed in vacuo and residue is taken in 1M sodium bicarbonate and extracted with ethyl acetate or dichloromethane. Extracts are washed with brine, dried over anhydrous sodium sulfate and then concentrated in vacuo. Derivatives of highly sulfonated dyes that have little or no solubility in dichloromethane or ethyl acetate are purified by reversed phase HPLC after the reaction is complete concentrated and/or lyophilized.

Conjugation to Antibodies

Dye-PC-NHS ester (~5-10 equivalent depending upon the dye loading desired) in DMSO (~5-10 mg/ml) is added to a solution of antibody in a mixture of PBS and 0.1M sodium bicarbonate/carbonate buffer at pH 8.5. Reaction mixture is stirred at room temperature for 30-60 minutes. Crude conjugate is purified on a NAP-5 or NAP-10 column depending upon the amount of conjugate prepared.

Synthesis of Dyes with Cleavable Disulfide Linker (Dye-SS-Py)

An amine functionalized dye (e.g. 4'-aminomethyl fluorescein) or an amine functionalized caged dye (prepared by reaction of CMNB caged carboxyfluorescein-NHS ester with excess diaminohexane) is conjugated to commercial available PEG12-SPDP (a heterobifunctional crosslinker with an NHS and a thiol reactive groups) at pH 7.5 in phosphate buffer. Crude solution is used as such in subsequent coupling to reduced antibodies as described below.

Conjugation of Antibodies to Dye-SS-Py

Antibody is reduced with DTT or TCEP (3-8 equivalent) depending upon the dye loading required and desalted twice to remove excess reducing agent. Reducing agent-free, reduced antibody is mixed with the Dye-SS-Py (various equivalent depending upon the dye to antibody ratio desired and coupling efficiency of different Dye-SS-Py reagents) in pH 7-8 buffer and incubated for 30-60 minutes. Coupling may be monitored by measuring amount of pyridine-2-thione released by recording its absorbance at 343 nm. After desired level of reaction, antibody conjugate is purified on a size exclusion column, NAP-5 or NAP-10.

Synthesis of Maleimide Modified Non-Cleavable Dyes (Dye-M)

An amine modified dye (masked, e.g. 4'(5')-aminomethyl-3'(6')-ethylfluorescein 6'(3')-phosphate prepared by deprotection of corresponding TFA protected derivative (Kumar & Sood US patent application US20120208223 A1) with base or an unmasked dye, e.g. 4'-aminomethylfluorescein) is modified with a non-cleavable bifunctional linker (e.g. sulfo-SMCC) in a process similar to 1.4. The crude product is purified by size-exclusion chromatography.

Conjugation of Antibodies to Dye-M

Antibody is reduced with DTT or TCEP (3-8 equivalent) depending upon the dye loading required and desalted twice to remove excess reducing agent. Reducing agent-free, reduced antibody is mixed with the Dye-M (various equivalent depending upon the dye to antibody ratio desired and coupling efficiency of different Dye-M reagents) in pH 7-8 buffer and incubated for 30-60 minutes at room temperature. Crude mixture is purified by size exclusion chromatography. To give pure antibody conjugates.

Example 2

Synthesis of Nucleic Acid Probes with Cleavable Dyes

Conjugation of Dye-PC to 2'-Deoxyuridine Triphosphate

Dye-PC NHS ester (3 equivalents) dissolved in DMSO or other water miscible solvent is added to a solution of 5-(3-aminoallyl)-2'-deoxyuridine-5'-triphosphate in 0.1M sodium carbonate/bicarbonate buffer (pH 8.5). Mixture is stirred at room temperature for 2-3 h and crude reaction is purified by reversed-phase HPLC.

Incorporation of Dye-PC Labeled dUTP into Nucleic Acid Probes for FISH

Dye-PC labeled dUTP is incorporated into a FISH probe using standard nick translation method.

Alternate Approach to Dye-PC-Labeled FISH Probes

Aminoallyl-dUTP is incorporated into a FISH probe using standard nick translation method and then conjugated to Dye-PC-NHS ester as described above in example 2.1.

Example 3

Synthesis of Dye-SS Labeled Synthetic Oligonucleotide Probe

Synthesis of Thiol Modified Oligonucleotides

A 5'-disulfide modified oligonucleotide is synthesized using 1-O-DMT-hexyl-disulfide, 1'-[2-cyanoethyl)-(N,N-diisopropyl)]-phosphoramidite using automated oligonucleotide synthesis followed by deprotection of nucleoside bases and cleavage of oligonucleotide from the solid support. After purification by HPLC, the oligonucleotide is reduced with 100 mM DTT at room temperature for 30 minutes and then rapidly purified by size exclusion chromatography.

Conjugation of Dye-SS-Py to Thiol-Modified Oligonucleotides

Immediately after purification of thiol-modified nucleotide, Dye-SS-Py is conjugated to the oligonucleotide in a process similar to Dye-SS-Py conjugation to antibodies as described above.

Example 4 Multiplex detection of biomarkers on tissue by imaging one set of antibodies followed by cleavage of the label and simultaneous activation of another label for imaging.

A multitissue array or whole tissue section is subjected to standard deparaffinization, antigen retrieval and blocking steps prior to incubation with CMNB-caged fluorescein-SS-anti Ki67 conjugate, fluorescein-PC-anti-S6 conjugate, and a 4'(5')-aminomethyl-3'(6')-ethylfluorescein-phosphate conjugated anti-E-cadherin antibody at 5-10 ug/ml concentration in 3% BSA in 1×PBS for 30 minutes at room temperature. After incubation slide is washed with 1×PBS, 3×5 min and counterstained with DAPI, 1×5 minutes. Slide is rinsed with PBS 1×10 min and then coverslipped with a glycerol containing mounting medium and an antifade agent. Fluorescein and DAPI are imaged using band pass filters to cutoff any light below 400 nm to prevent linker cleavage or caged-dye activation. After imaging, dye is exposed to a 380 nm light for 5-60 minutes, to cleave the already imaged fluorescein and activate the CMNB-caged fluorescein by cleavage of CMNB mask. Slide is decoverslipped and washed with PBS. It is recoverslipped with same mounting media and imaged in the DAPI and fluorescein channels. After imaging the disulfide linker is cleaved with DTT and cleaved dye washed off in a fashion similar to that described above. Subsequently, slide is incubated with an alkaline phosphatase in phosphatase buffer for 5-15 minutes to activate the phosphate caged ethylfluorescein and tissue is reimaged after coverslipping in the same channels as in previous two rounds.

It should be noted that phosphate mask should only be cleaved after all the phosphoprotein targets have been detected.

Example 5

Combining Simultaneous Hybridization with Sequential Staining with Sequential Staining and Imaging to Achieve Even Higher Order Multiplexing After multiple rounds of imaging, slide from example 4 is subjected to photoactivated chemical bleaching as described in Sood et. al. US patent publication 20130165330A1 published Jun. 27, 2013, using a triphenylalkylborate as an electron transfer reagent. After bleaching slide is washed with 1×PBS, 3×5 min. and stained with a biotinylated anti-β-catenin antibody and fluorescein conjugated-SS-anti-EGFR antibody. After imaging, fluorescein is cleaved from the anti-EGFR antibody as described above in example 4 and the slide is stained with a fluorescein conjugated streptavidin to bind biotinylated anti-β-catenin antibody bound to its target in the tissue. After removal of excess streptavidin conjugate, slide is imaged in the DAPI and fluorescein channels.

Example 6

Detection of EGFR and cMET Amplification in NSCLC after Multiplex Protein Analysis To allow subsequent FISH staining on slide from Example 4 or 5 coverslip is removed by incubation in 2×SSC buffer and slide is subjected to 10 min treatment with 0.05% pepsin that partially removed protein structures to allow access to nuclear DNA. Slide is then fixed using aqueous 4% formaldehyde solution for 10 min, washed and subjected to hybridization using FISH probes for EGFR (Fluorescein-PC-EGFR probe), cMet (digoxigenin-cMET probe) and Chromosome 7 centromere (PlatinumBright415, aqua fluorophore) and counterstained with DAPI. The hybridization is carried out by dehydrating the slide by passage through series of aqueous solutions of increasing concentration of ethanol followed by 100% ethanol and then allowed to dry briefly. The probe mixture is applied on the region of the slide containing tissue section, then covered with a coverslip and placed in a slide incubator capable of heating and cooling the slide. The slide containing the probe mixture is heated to 80° C. for 10 min to denature DNA hybrids and allowed to cool to 37° C. The slide is then kept at that temperature for 16 hours. Slide is then washed in 2×SSC buffer containing 0.3% of detergent NP-40 and washed 2 min in 0.4×SSC containing 0.3% NP-40 at 72° C. followed by counterstaining with DAPI. Next, the regions of tissue section that had invasive tumor are imaged using coordinates recorded in the immunofluorescence step in examples 4 or 5. Image sets are recorded at 40× using filter sets specific to aqua, green and DAPI. After imaging EGFR and Centromere 7 probes, tissue section is washed with 2×SCC and incubated with DTT in 2×SCC to remove fluorescein tag. After washing with 2×SCC, section is stained with fluorescein-conjugated anti-digoxigenin antibody to stain the cMET probe bound to its target and reimaged in the green and DAPI channels.

Example 7

Detection of U6 snRNA and b-Actin mRNA Using Fluorescein-SS-b-Actin Probe and Biotin-U6 Probe Preparation of Tissue Samples Paraffin embedded tissue or cell pellet slides are baked at 60° C. for one hour with tissue facing up and parallel to the oven rack. After baking, slides are deparaffinized by washing in xylene with gentle agitation for ten minutes. The samples are then rehydrated by washing in four solutions of ethanol with concentrations decreasing in the order of 100%, 95%, 70%, and 50% followed by a wash with 1× phosphate buffer saline (PBS, pH 7.4). After rehydration, the slides are washed with 1×PBS. A ten minute wash in 0.3% Triton X-100 in PBS is performed for membrane permeabilization of the tissue, followed by a wash with 1×PBS.

U6 snRNA and β-Actin Detection

After permeabilization, slides are incubated with prehybridization buffer (1× Exiqon buffer, Exiqon, miRCURY LNA™ microRNA ISH Optimization Kit) for one hour at room temperature then hybridized with 1000 of solution containing 25 mM each of Fluorescein-SS-β-Actin and Biotin-U6 LNA (locked nucleic acid) probes in Exiqon buffer at 50° C. overnight in Thermobrite. Slides are washed with 0.5×SSC and 0.2×SSC at 50° C. for 10 min then rinsed with 0.1×SSC briefly. Slides are DAPI stained at room temperature for 15 min and mounted with a mounting medium. The images are taken on Olympus microscope with a 20× objective. After β-actin imaging, coverslips are removed by incubating the slides in 0.5×SCC at room temperature. Fluorescein is cleaved off the samples by incubation with 100 mM DTT in 0.5×SCC and samples are washed with 0.5×SCC at room temperature. Slides are then stained with fluorescein-conjugated streptavidin to detect the biotinylated U6 probe bound to its target by reimaging in the fluorescein channel.

While the examples described above used only a xanthene dye to demonstrate the use of same imaging channel to detect multiple markers by simultaneous hybridization of antibodies, multiple classes of dyes can be masked and can similarly be attached to antibodies or nucleic acid probes and used. Examples 4 & 5 together describe a combination of approaches where higher order multiplexing is achieved by simultaneous hybridization of one set of antibodies and multiple dye-cleavage and activation cycles (approach 1, example 4) to image a large set of markers not ordinarily possible in a single cycle as well as multiple rounds of antibody staining and signal removal (approach 2, example 3).

What is claimed is:

1. A method of probing multiple targets in a biological sample comprising:
    (a) providing a biological sample containing multiple targets;
    (b) binding a set of probes to the multiple targets wherein two or more of the probes in said set of probes comprises independently:
        a binder capable of specific binding to at least one target in the biological sample;
        a signal generator (SG) capable of providing a detectable signal using one or more detection techniques;
        a linker which couples the SG to the binder;
        a masking agent coupled to the SG to which, when coupled to the SG, quenches the signal of the SG; and
        wherein at least one linker and one masking agent in the set of probes are linker-mask pairs; and
        the number of probes comprising each set is defines as:

$P_x = SG_y * (OP_z + 1)$ wherein x, y, and z are integers; and
            x is the number of probes comprising a specific binder;
            y is the number of signal generators (SG); and
            z is the number of orthogonal linker-mask pairs (OP);
    (c) detecting at least one signal from at least one signal generator from the set of probes bound in step (b);
    (d) contacting the sample comprising the bound probes of step (b) with a chemical agent, electromagnetic radiation, or a combination thereof and simultaneously deactivating the at least one signal generator detected in step (c) by cleavage of a linker bound to said signal generator and activating at least one signal generator from the set of probes previously quenched by a masking agent wherein the linker and masking agent are linker-mask pairs;
    (e) detecting at least one signal from the activation of the at least one newly activated signal generators in step (d);
    (f) contacting the sample comprising the bound probes of the prior step with a chemical agent or electromagnetic radiation or a combination of both and simultaneously deactivating the at least one signal generator detected in the prior step by cleavage of a linker bound to said signal generator and activating at least one signal generator previously quenched by a masking agent wherein the linker and masking agent are orthogonal linker-mask pairs;
    (g) detecting at least one signal from the activation of the at least signal generator in step (f); and
    (h) optionally repeating steps (f)-(g).

2. The method of claim 1 wherein the binder comprises at least one antibody.

3. The method of claim 1, wherein at least one signal generator comprises an optical signal generator, and at least one signal detected in steps (c), (e), or (f) is an optical signal.

4. The method of claim 1, wherein at least one signal generator comprises a fluorescent signal generator, and at least one signal detected in steps (c), (e), or (f) is a fluorescent signal.

5. The method of claim 4, wherein the fluorescent signal generator comprises a xanthene dye.

6. The method of claim 5, wherein the xanthene dye is a fluorescein or rhodamine dye.

7. The method of claim 4, wherein the fluorescent signal generator comprises a cyanine dye.

8. The method of claim 7, wherein the cyanine dye is Cy3 or Cy5.

9. The method of claim 1, wherein detecting at least one signal in steps (c), (e), or (f) is accomplished by exposing the sample to light of 300 nm-1.3 µM in wavelength.

10. The method of claim 9, wherein detecting a signal in steps (c), (e), or (f) is accomplished by exposing the sample to light of 300-700 nm in wavelength.

11. The method of claim 1 wherein detecting at least one signal in steps (c), (e), or (f) comprises detection of the signal in a same channel.

12. The method of claim 1, wherein a chemical agent and a photoactivated chemical bleaching agent is used independently at least once.

13. The method of claim 12 wherein the photoactivated chemical bleaching agent is activated by irradiating the sample after contacting the sample with said photoactivated chemical bleaching agent.

14. The method of claim 1, wherein the steps (d) and (f) are performed for about 20 seconds to about 15 minutes.

15. The method of claim 1, further comprising measuring one or more intensity values of the signal detected in detecting step (c), step (g), or steps (c) and (g).

16. The method of claim 15, further comprising correlating the intensity value with an amount of target present in the sample.

17. The method of claim 1, wherein steps (b)-(g) are repeated one or more times.

18. The method of claim 17 wherein in total x is an integer between 2 and 100, y is an integer between 2 and 20, and z is an integer between 1 and 25.

19. The method of claim 18 wherein x is an integer between 10 and 80, y is an integer between 2 and 10, and z is an integer between 2 and 10.

20. The method of claim 18 wherein x is an integer between 12 and 50, y is an integer between 3 and 6, and z is an integer between 2 and 5.

21. The method of claim 1 wherein at least one signal generator in detecting step (c), (e), and (g) are detected using a an electron spin resonance (ESR) detection system, a charge coupled device (CCD) detection system, a fluorescent detection system, an electrical detection system, a photographic film detection system, a chemiluminescent detection system, an enzyme detection system, an atomic force microscopy (AFM) detection system, a scanning tunneling microscopy (STM) detection system, an optical detection system, a near field detection system, or a total internal reflection (TIR) detection system.

* * * * *